United States Patent
Begin et al.

(10) Patent No.: US 9,307,926 B2
(45) Date of Patent: Apr. 12, 2016

(54) AUTOMATIC STENT DETECTION

(71) Applicant: VOLCANO CORPORATION, San Diego, CA (US)

(72) Inventors: Elizabeth Begin, Billerica, MA (US); Nathaniel J. Kemp, Concord, MA (US); Jason Sproul, Watertown, MA (US); Badr Elmaanaoui, Billerica, MA (US)

(73) Assignee: Volcano Corporation, San Diego, CA (US)

( * ) Notice: Subject to any disclaimer, the term of this patent is extended or adjusted under 35 U.S.C. 154(b) by 247 days.

(21) Appl. No.: 14/044,441

(22) Filed: Oct. 2, 2013

(65) Prior Publication Data

US 2014/0100449 A1   Apr. 10, 2014

Related U.S. Application Data

(60) Provisional application No. 61/710,429, filed on Oct. 5, 2012.

(51) Int. Cl.
*G06K 9/00* (2006.01)
*A61B 5/06* (2006.01)
(Continued)

(52) U.S. Cl.
CPC .............. *A61B 5/061* (2013.01); *A61B 5/0066* (2013.01); *A61B 5/0073* (2013.01);
(Continued)

(58) Field of Classification Search
CPC .... A61B 5/0066; A61B 5/0073; A61B 5/061; A61B 8/0841; A61B 8/12; A61B 8/14; A61B 8/4416; A61B 8/5223; A61B 8/5261; G06K 9/6247; G06T 2207/10072; G06T 2207/10136; G06T 2207/20048; G06T 2207/20081; G06T 2207/30101; G06T 7/0044
See application file for complete search history.

(56) References Cited

U.S. PATENT DOCUMENTS 3,301,258 A   1/1967   Werner
3,617,880 A   11/1971  Cormack et al.
(Continued)

FOREIGN PATENT DOCUMENTS

EP   1041373 A2    10/2000
EP   01172637 A1   1/2002
(Continued)

OTHER PUBLICATIONS

Sihan et al., 2008, A novel approach to quantitative analysis of intraluminal optical coherence tomography imaging, Comput. Cardiol:1089-1092.
(Continued)

*Primary Examiner* — Tom Y Lu
(74) *Attorney, Agent, or Firm* — Brown Rudnick LLP; Thomas C. Meyers

(57) ABSTRACT

This invention relates generally to the detection of objects, such as stents, within intraluminal images using principal component analysis and/or regional covariance descriptors. In certain aspects, a training set of pre-defined intraluminal images known to contain an object is generated. The principal components of the training set can be calculated in order to form an object space. An unknown input intraluminal image can be obtained and projected onto the object space. From the projection, the object can be detected within the input intraluminal image. In another embodiment, a covariance matrix is formed for each pre-defined intraluminal image known to contain an object. An unknown input intraluminal image is obtained and a covariance matrix is computed for the input intraluminal image. The covariances of the input image and each image of the training set are compared in order to detect the presence of the object within the input intraluminal image.

33 Claims, 17 Drawing Sheets

(51) Int. Cl.
*A61B 5/00* (2006.01)
*A61B 8/08* (2006.01)
*A61B 8/12* (2006.01)
*G06T 7/00* (2006.01)
*G06K 9/62* (2006.01)
*A61B 8/14* (2006.01)
*A61B 8/00* (2006.01)

(52) U.S. Cl.
CPC .............. *A61B 8/0841* (2013.01); *A61B 8/12* (2013.01); *A61B 8/5261* (2013.01); *G06K 9/6274* (2013.01); *G06T 7/0044* (2013.01); *A61B 8/14* (2013.01); *A61B 8/4416* (2013.01); *A61B 8/5223* (2013.01); *G06T 2207/10072* (2013.01); *G06T 2207/10136* (2013.01); *G06T 2207/20048* (2013.01); *G06T 2207/20081* (2013.01); *G06T 2207/30101* (2013.01)

(56) References Cited

U.S. PATENT DOCUMENTS

| | | |
|---|---|---|
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |

(56) References Cited

U.S. PATENT DOCUMENTS

| | | |
|---|---|---|
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |

(56) References Cited

U.S. PATENT DOCUMENTS

| | | |
|---|---|---|
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |

(56) References Cited

U.S. PATENT DOCUMENTS

| | | |
|---|---|---|
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,025,622 B2 * | 9/2011 | Rold et al. .................. 600/463 |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0049375 A1 * | 4/2002 | Strommer et al. ............ 600/407 |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |

(56) References Cited

U.S. PATENT DOCUMENTS

| | | |
|---|---|---|
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1* | 11/2005 | Kimmel ............ G06T 7/0081 382/128 |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187462 A1* | 8/2006 | Srinivasan et al. ............ 356/479 |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1* | 7/2007 | Unal ............ A61B 5/0066 600/407 |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |

(56) References Cited

U.S. PATENT DOCUMENTS

| | | |
|---|---|---|
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg |
| 2012/0004529 A1 | 1/2012 | Tolkowsky et al. |
| 2012/0004668 A1 | 1/2012 | Wallace et al. |

(56) References Cited

U.S. PATENT DOCUMENTS

| | | |
|---|---|---|
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/44296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |

(56) References Cited

FOREIGN PATENT DOCUMENTS

| | | | |
|---|---|---|---|
| WO | 2008/107905 | A2 | 9/2008 |
| WO | 2009/009799 | A1 | 1/2009 |
| WO | 2009/009801 | A1 | 1/2009 |
| WO | 2009/046431 | A1 | 4/2009 |
| WO | 2009/121067 | A1 | 10/2009 |
| WO | 2009/137704 | A1 | 11/2009 |
| WO | 2011/006886 | A2 | 1/2011 |
| WO | 2011/038048 | A1 | 3/2011 |
| WO | 2011/081688 | A1 | 7/2011 |
| WO | 2012/003369 | A2 | 1/2012 |
| WO | 2013/033414 | A1 | 3/2012 |
| WO | 2012/061935 | A1 | 5/2012 |
| WO | 2012/071388 | A2 | 5/2012 |
| WO | 2012/087818 | A1 | 6/2012 |
| WO | 2012/098194 | A1 | 7/2012 |
| WO | 2012/109676 | A1 | 8/2012 |
| WO | 2012/130289 | A1 | 10/2012 |
| WO | 2012/154767 | A2 | 11/2012 |
| WO | 2012/155040 | A1 | 11/2012 |
| WO | 2013/033415 | A2 | 3/2013 |
| WO | 2013/033418 | A1 | 3/2013 |
| WO | 2013/033489 | A1 | 3/2013 |
| WO | 2013/033490 | A1 | 3/2013 |
| WO | 2013/033592 | A1 | 3/2013 |
| WO | 2013/126390 | A1 | 8/2013 |
| WO | 2014/109879 | A1 | 7/2014 |

OTHER PUBLICATIONS

Siwy et al., 2003, Electro-responsive asymmetric nanopores in polyimide with stable ion-current signal, Applied Physics A: Materials Science & Processing 76:781-785.

Smith et al., 1989, Absolute displacement measurements using modulation of the spectrum of white light in a Michelson interferometer, Applied Optics, 28(16):3339-3342.

Smith, 1997, The Scientist and Engineer's Guide to Digital Signal Processing, California Technical Publishing, San Diego, CA:432-436.

Soller, 2003, Polarization diverse optical frequency domain interferometry:All coupler implementation, Bragg Grating, Photosensitivity, and Poling in Glass Waveguides Conference MB4:30-32.

Song et al., 2012, Active tremor cancellation by a "Smart" handheld vitreoretinal microsurgical tool using swept source optical coherence tomography, Optics Express, 20(21):23414-23421.

Stenqvist et al., 1983, Stiffness of central venous catheters, Acta Anaesthesiol Scand., 2:153-157.

Strickland, 1970, Time-Domain Reflectometer Measurements, Tektronix, Beaverton, OR, (107 pages).

Strobl et al., 2009, An Introduction to Recursive Partitioning:Rationale, Application and Characteristics of Classification and Regression Trees, Bagging and Random Forests, Psychol Methods., 14(3):323-348.

Sutcliffe et al., 1986, Dynamics of UV laser ablation of organic polymer surfaces, Journal of Applied Physics, 60(9):3315-3322.

Suzuki, 2013, A novel guidewire approach for handling acute-angle bifurcations, J Inv Cardiol 25(1):48-54.

Tanimoto et al., 2008, A novel approach for quantitative analysis of intracoronary optical coherence tomography: high inter-observer agreement with computer-assisted contour detection, Cathet Cardiovascular Intervent., 72(2):228-235.

Tearney et al., 1997, In vivo Endoscopic Optical Biopsy with Optical Coherence Tomography, Science, 276:2037-2039.

Tonino et al., 2009, Fractional flow reserve versus angiography for guiding percutaneous coronary intervention, The New England Journal of Medicine, 360:213-224.

Toregeani et al., 2008, Evaluation of hemodialysis arteriovenous fistula maturation by color-flow Doppler ultrasound, J Vasc. Bras. 7(3):203-213.

Translation of Notice of Reason(s) for Refusal dated Apr. 30, 2014, for Japanese Patent Application No. 2011-508677, (5 pages).

Translation of Notice of Reason(s) for Refusal dated May 25, 2012, for Japanese Patent Application No. 2009-536425, (3 pages).

Translation of Notice of Reason(s) for Refusal dated Nov. 22, 2012, for Japanese Patent Application No. 2010-516304, (6 pages).

Traunecker et al., 1991, Bispecific single chain molecules (Janusins) target cytotoxic lymphocytes on HIV infected cells, EMBO J., 10:3655-3659.

Trolier-McKinstry et. al., 2004, Thin Film Piezoelectric for MEMS, Journal of Electroceramics 12:7-17.

Tuniz et al., 2010, Weaving the invisible thread: design of an optically invisible metamaterial fibre, Optics Express 18 (17):18095-18105.

Turk et al., 1991, Eigenfaces for Recognition, Journal of Cognitive Neuroscience 3(1):71-86.

Tuzel et al., 2006, Region Covariance: A Fast Descriptor for Detection and Classification, European Conference on Computer Vision (ECCV).

Urban et al., 2010, Design of a Pressure Sensor Based on Optical Bragg Grating Lateral Deformation, Sensors (Basel), 10(12):11212-11225.

Vakhtin et al., 2003, Common-path interferometer for frequency-domain optical coherence tomography, Applied Optics, 42(34):6953-6958.

Vakoc et al., 2005, Phase-Resolved Optical Frequency Domain Imaging, Optics Express 13(14):5483-5493.

Verhoeyen et al., 1988, Reshaping human antibodies: grafting an antilysozyme activity, Science, 239:1534-1536.

Villard et al., 2002, Use of a blood substitute to determine instantaneous murine right ventricular thickening with optical coherence tomography, Circulation, 105:1843-1849.

Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).

Wang et al., 2006, Multiple biomarkers for the prediction of first major cardiovascular events and death, The New England Journal of Medicine, 355(25):2631-2639.

Wang et al., 2009, Robust Guidewire Tracking in Fluoroscopy, IEEE Conference on Computer Vision and Pattern Recognition—CCPR 2009:691-698.

Wang et al., 2011, In vivo intracardiac optical coherence tomography imaging through percutaneous access: toward image-guided radiofrequency ablation, J. Biomed. Opt. 0001 16(11):110505-1 (3 pages).

Waterhouse et. al., 1993, Combinatorial infection and in vivo recombination: a strategy for making large phage antibody repertoires, Nucleic Acids Res., 21:2265-2266.

Wegener, 2011, 3D Photonic Metamaterials and Invisibility Cloaks: The Method of Making, MEMS 2011, Cancun, Mexico, Jan. 23-27, 2011.

West et al., 1991, Arterial insufficiency in hemodialysis access procedures: correction by banding technique, Transpl Proc 23(2):1838-40.

Wyawahare et al., 2009, Image registration techniques: an overview, International Journal of Signal Processing, Image Processing and Pattern Recognition, 2(3):11-28.

Yaqoob et al., 2006, Methods and application areas of endoscopic optical coherence tomography, J. Biomed. Opt., 11, 063001-1-063001-19.

Yasuno et al., 2004, Polarization-sensitive complex Fourier domain optical coherence tomography for Jones matrix imaging of biological samples, Applied Physics Letters 85(15):3023-3025.

Zhang et al., 2004, Full range polarization-sensitive Fourier domain optical coherence tomography, Optics Express, 12(24):6033-6039.

Zitova et al., 2003, Image registration methods: A survey. Image and Vision Computing, 21(11):977-1000.

Abdi et al., 2010, Principal component analysis, Wiley Interdisciplinary Reviews: Computational Statistics 2:433-459.

Adler et al., 2007, Phase-Sensitive Optical Coherence Tomography at up to 370,000 Lines Per Second Using Buffered Fourier Domain Mode-Locked Lasers, Optics Letters, 32(6):626-628.

Agresti, 1996, Models for Matched Pairs, Chapter 8, An Introduction to Categorical Data Analysis, Wiley-Interscience A John Wiley & Sons, Inc., Publication, Hoboken, New Jersey.

(56) References Cited

OTHER PUBLICATIONS

Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intel. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring—the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.

Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61 (1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radio-frequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion mailed Mar. 11, 2014, for International Patent Application No. PCT/US13/75675, filed Dec. 17, 2013 (7 pages).
International Search Report and Written Opinion mailed Mar. 19, 2014, for International Patent Application No. PCT/US13/075353, filed Dec. 16, 2013 (8 pages).
International Search Report and Written Opinion mailed Nov. 2, 2012, for International Patent Application No. PCT/US12/53168, filed Aug. 30, 2013 (8 pages).
International Search Report and Written Opinion mailed on Apr. 14, 2014, for International Patent Application No. PCT/US2013/076148, filed Dec. 18, 2013 (8 pages).
International Search Report and Written Opinion mailed on Apr. 21, 2014, for International Patent Application No. PCT/US2013/076015, filed Dec. 18, 2013 (7 pages).
International Search Report and Written Opinion mailed on Apr. 23, 2014, for International Patent Application No. PCT/US2013/075328, filed Dec. 16, 2013 (8 pages).
International Search Report and Written Opinion mailed on Apr. 29, 2014, for International Patent Application No. PCT/US13/76093, filed Dec. 18, 2013 (6 pages).

(56) References Cited

OTHER PUBLICATIONS

International Search Report and Written Opinion mailed on Apr. 9, 2014, for International Patent Application No. PCT/US13/75089, filed Dec. 13, 2013 (7 pages).
International Search Report and Written Opinion mailed on Feb. 21, 2014, for International Patent Application No. PCT/US13/76053, filed Dec. 18, 2013 (9 pages).
International Search Report and Written Opinion mailed on Feb. 21, 2014, for International Patent Application No. PCT/US2013/076965, filed Dec. 20, 2013 (6 pages).
International Search Report and Written Opinion mailed on Feb. 27, 2014, for International Patent Application No. PCT/US13/75416, filed Dec. 16, 2013 (7 pages).
International Search Report and Written Opinion mailed on Feb. 28, 2014, for International Patent Application No. PCT/US13/75653, filed Dec. 17, 2013 (7 pages).
International Search Report and Written Opinion mailed on Feb. 28, 2014, for International Patent Application No. PCT/US13/75990, filed Dec. 18, 2013 (7 pages).
International Search Report and Written Opinion mailed on Jan. 16, 2009, for International Patent Application No. PCT/US08/78963 filed on Oct. 6, 2008 (7 pages).
International Search Report and Written Opinion mailed on Jul. 30, 2014, for International Patent Application No. PCT/US14/21659, filed Mar. 7, 2014 (15 pages).
International Search Report and Written Opinion mailed on Mar. 10, 2014, for International Patent Application No. PCT/US2013/076212, filed Dec. 18, 2013 (8 pages).
International Search Report and Written Opinion mailed on Mar. 11, 2014, for International Patent Application No. PCT/US13/76173, filed Dec. 16, 2013 (9 pages).
International Search Report and Written Opinion mailed on Mar. 11, 2014, for International Patent Application No. PCT/US13/76449, filed Dec. 19, 2013 (9 pages).
International Search Report and Written Opinion mailed on Mar. 18, 2014, for International Patent Application No. PCT/US2013/076502, filed Dec. 19, 2013 (7 pages).
International Search Report and Written Opinion mailed on Mar. 18, 2014, for International Patent Application No. PCT/US2013/076788, filed Dec. 20, 2013 (7 pages).
International Search Report and Written Opinion mailed on Mar. 19, 2014, for International Patent Application No. PCT/US13/75349, filed Dec. 16, 2013 (10 pages).
International Search Report and Written Opinion mailed on Mar. 19, 2014, for International Patent Application No. PCT/US2013/076587, filed Dec. 19, 2013 (10 pages).
International Search Report and Written Opinion mailed on Mar. 19, 2014, for International Patent Application No. PCT/US2013/076909, filed Dec. 20, 2013 (7 pages).
International Search Report and Written Opinion mailed on Mar. 7, 2014, for International Patent Application No. PCT/US2013/076304, filed Dec. 18, 2013 (9 pages).
International Search Report and Written Opinion mailed on Mar. 7, 2014, for International Patent Application No. PCT/US2013/076480, filed Dec. 19, 2013 (8 pages).
International Search Report and Written Opinion mailed on Mar. 7, 2014, for International Patent Application No. PCT/US2013/076512, filed Dec. 19, 2013 (8 pages).
International Search Report and Written Opinion mailed on Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.
Machine translation of JP 2000-097846.
Machine translation of JP 2000-321034.
Machine translation of JP 2000-329534.
Machine translation of JP 2004-004080.
Maintz et al., 1998, An Overview of Medical Image Registration Methods, Technical Report UU-CS, (22 pages).

(56) References Cited

OTHER PUBLICATIONS

Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Source in the Telescope-Less Configurations with Application in Optical Coherence Tomography, Optics Letters 33(15):1741-1743.
Nissen, 2001, Coronary Angiography and Intravascular Ultrasound, American Journal of Cardiology, 87 (suppl):15A-20A.
Nitenberg et al., 1995, Coronary vascular reserve in humans: a critical review of methods of evaluation and of interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26 (1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4)1 547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vase Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.

* cited by examiner

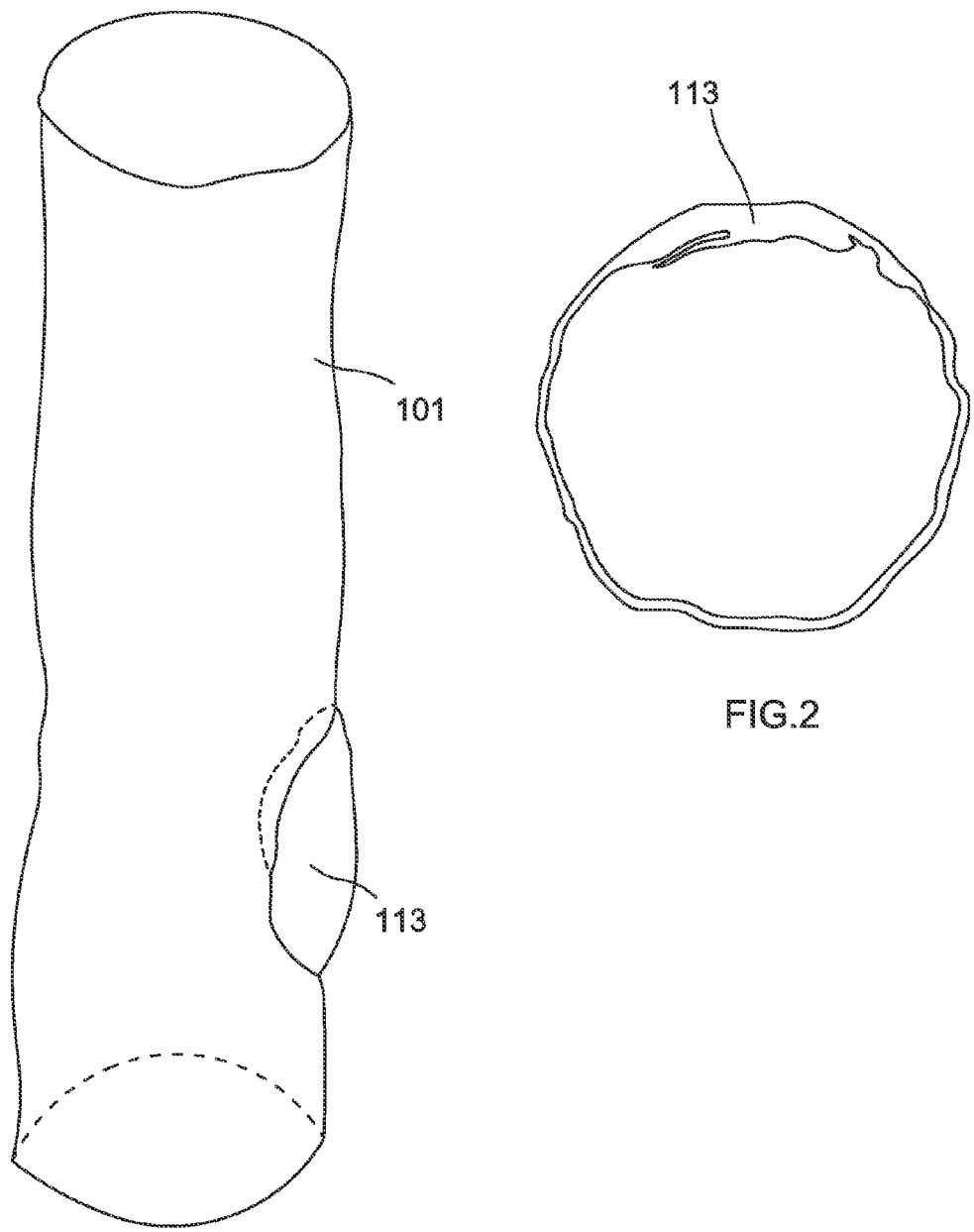

Figure 16
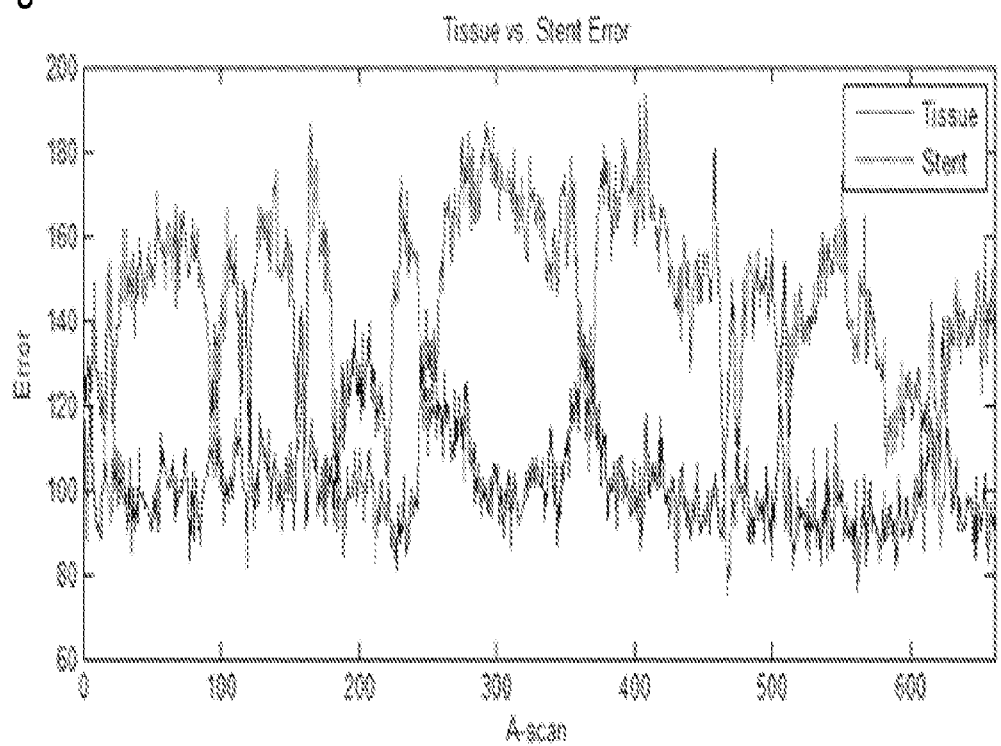
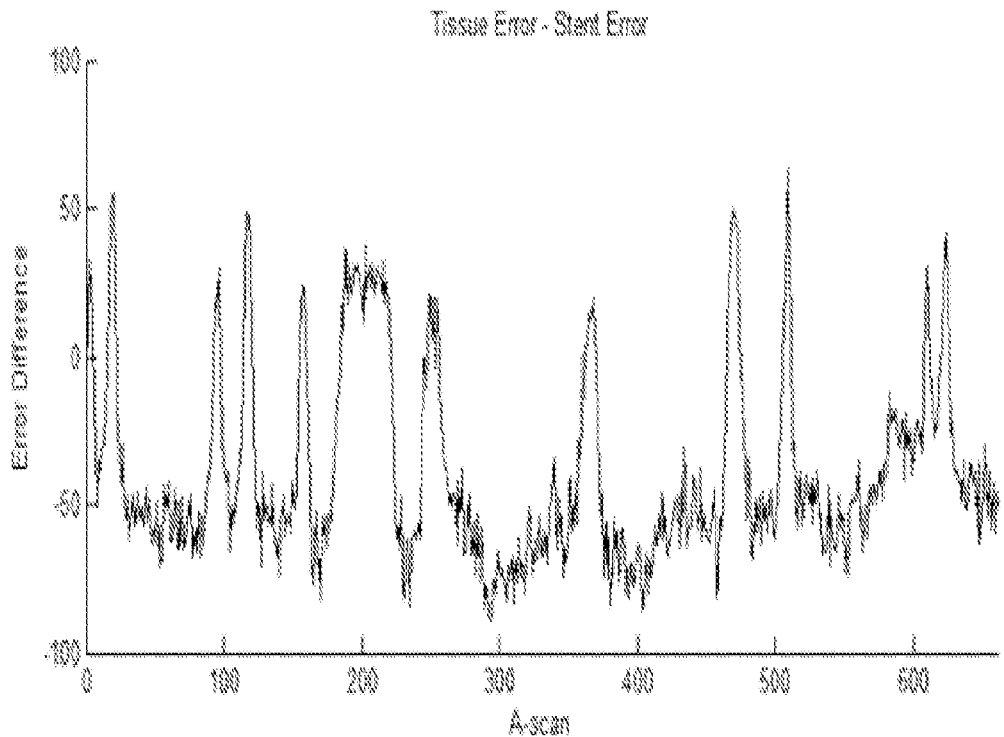

AUTOMATIC STENT DETECTION

RELATED APPLICATION

This application claims the benefit of and priority to U.S. Provisional No. 61/710,429, filed Oct. 5, 2012, which is incorporated by reference in its entirety.

TECHNICAL FIELD

This invention generally relates to the automatic detection of stents in intraluminal imaging.

BACKGROUND

Tomographic imaging is a signal acquisition and processing technology that allows for high-resolution cross-sectional imaging in biological systems. Tomographic imaging systems include, for example, optical coherence tomography systems, ultrasound imaging systems, and computed tomography. Tomographic imaging is particularly well-suited for imaging the subsurface of a vessel or lumen within the body, such as a blood vessel, using probes disposed within a catheter through a minimally invasive procedure.

Typical tomographic imaging catheters consist of an imaging core that rotates and moves longitudinally through a blood vessel, while recording an image video loop of the vessel. The motion results in a 3D dataset, where each frame provides a 360 degree slice of the vessel at different longitudinal section. These frames provide cardiologists with invaluable information such as the location and severity of the stenosis in a patient, the presence of vulnerable plagues, and changes in the disease over time. The information also assists in determining the appropriate treatment plan for the patient, such as drug therapy, stent placement, angioplasty, or bypass surgery.

One of the most common analyses performed is the placement and apposition of stents. A stent is a small, typically meshed or slotted, tube-like structure made of a metal or polymer that is inserted into the blood vessel to hold vessel open and keep it from occluding and provides a framework for arterial lesions that are likely to embolize after balloon angioplasty. During placement, the stent should be placed in parallel within the vessel and contact the vessel wall. Apposition of a coronary artery stent is the term for how well stent lies against the wall of the artery. When the stent as placed does not mesh completely against the blood vessel, the stent is in 'incomplete apposition'. Incomplete apposition may raise the risk of a subsequent blockage or thrombus because of blood pooling or stagnating in the dead space between the stent and the coronary artery wall. Therefore, it is critical to verify that the stent is properly employed.

In order to identify and measure stent opposition in intravascular images, a cardiologist typically has to manually locate the stent struts, which are the framework of the stent visible in the tomographic image. Generally, identification of at least two stent struts is required to determine stent apposition. This process can be a very time consuming and is prone to user error.

SUMMARY

This invention generally improves the ability of user of a tomographic imaging system to quickly assess a deployed stent by providing a method for detecting the stent location. Through use of the image processing techniques, the stent locations for all frames or a subset of frames in a recorded dataset for an imaging run are detected and provided to the user. The resulting stent detections may be displayed on the tomographic image, the image longitudinal display (ILD) or displayed on 3-D reconstructions of the vessel. This advantageously eliminates the need for the user to manually locate the stent struts in order to quantify the apposition. Moreover, automatically detecting stents reduces error associated with manual detection and provides a more reliable means to detect and remedy mal-apposed stents.

Tomographic imaging systems suitable for use in aspects of the invention include any tomographic cross-sectional imaging system capable of obtaining intraluminal images, such as optical coherence tomography systems, ultrasound imaging systems and combined OCT-ultrasound imaging systems. Intraluminal images are typically intravascular images, but also include any image taken within a biological lumen, such as an intestinal lumen.

This invention relates to computing systems and methods for computer-assisted detection of a stent, a stent strut, or a portion of the stent, and can also be used to detect other objects within intraluminal images such as tissue or a guidewire. Objects are identified based on the locations in the polar coordinate system using data obtained from one-dimensional, two dimensional or three-dimensional images. Once stent struts are identified, measurements of the stent apposition or coverage relative to the lumen border can be easily computed.

In one aspect, a set of pre-defined intraluminal images that are known to display a object are generated to train a processor to identify or recognize the object in intraluminal images unknown to contain the object, for example, input intraluminal images of a patient undergoing an OCT examination. For example, in this step, a set of pre-defined intraluminal data images can include a plurality of intraluminal images known to display a stent strut so that a processor can be trained to identify the stent strut. After a training set of the pre-defined intraluminal images is generated, the principal components for the set can be computed to create an object space for the object. The principal components for the object can be stored and used to detect the object in input intraluminal images that are unknown to contain the object. By projecting the input intraluminal image onto the object space, the object can be detected within the input intraluminal image.

In certain embodiments, after the input intraluminal image is projected onto the object space, the error, for example, the Euclidean distance, between the input intraluminal image and the object space image is determined. A small error can constitute a positive detection of the object within input intraluminal image. The image can then be post-processed to identify or highlight the detected object within the input intraluminal image. Post-processing can also include removing false object detections from the input intraluminal image.

In some embodiments, at least two sets of pre-defined intraluminal images known to display different objects are generated, for example, a set of pre-defined intraluminal images known to display stents and a set of pre-defined intraluminal images known to display tissue. The principal components for each set can be computed to generate an object space for each object. An input intraluminal image unknown to display either object is projected onto each object space and the objects are detected within the input intraluminal images. The objects can be detected by calculating an error between the input intraluminal image and each object space. The object space that most accurately represents the input intraluminal image, for example, has the smallest error, is indicative of a positive detection of the corresponding object to the object space. The object space with the larger error can be indicative of a negative detection for its corresponding object. This advantageously increases the accuracy of the detection because instead of detecting based on error alone, detection is based on the combination of error and a comparison of the errors.

In another aspect, an object, such as stent, can be detected within an input intraluminal image by generating a training set of intraluminal images of an object, where each image is defined by one or more features. A covariance matrix can be computed for a feature within each pre-defined intraluminal image of the training set. The covariance for a feature within the input intraluminal image can be calculated and compared to the covariances of the training set. From the comparison, the object can be detected within the input intraluminal image. In certain aspects, the feature can be the Cartesian coordinates of a pixel, the intensity at each pixel, or the first and second order derivatives of the image in the x and y direction.

Other and further aspects and features of the invention will be evident from the following detailed description and accompanying drawings, which are intended to illustrate, not limit, the invention.

BRIEF DESCRIPTION OF DRAWINGS

FIG. 1 is a perspective view of a vessel.
FIG. 2 is a cross sectional view of the vessel shown in FIG. 1.
FIG. 16 depicts the error of projected data using stent and tissue principal components.

DESCRIPTION

Figure 3:
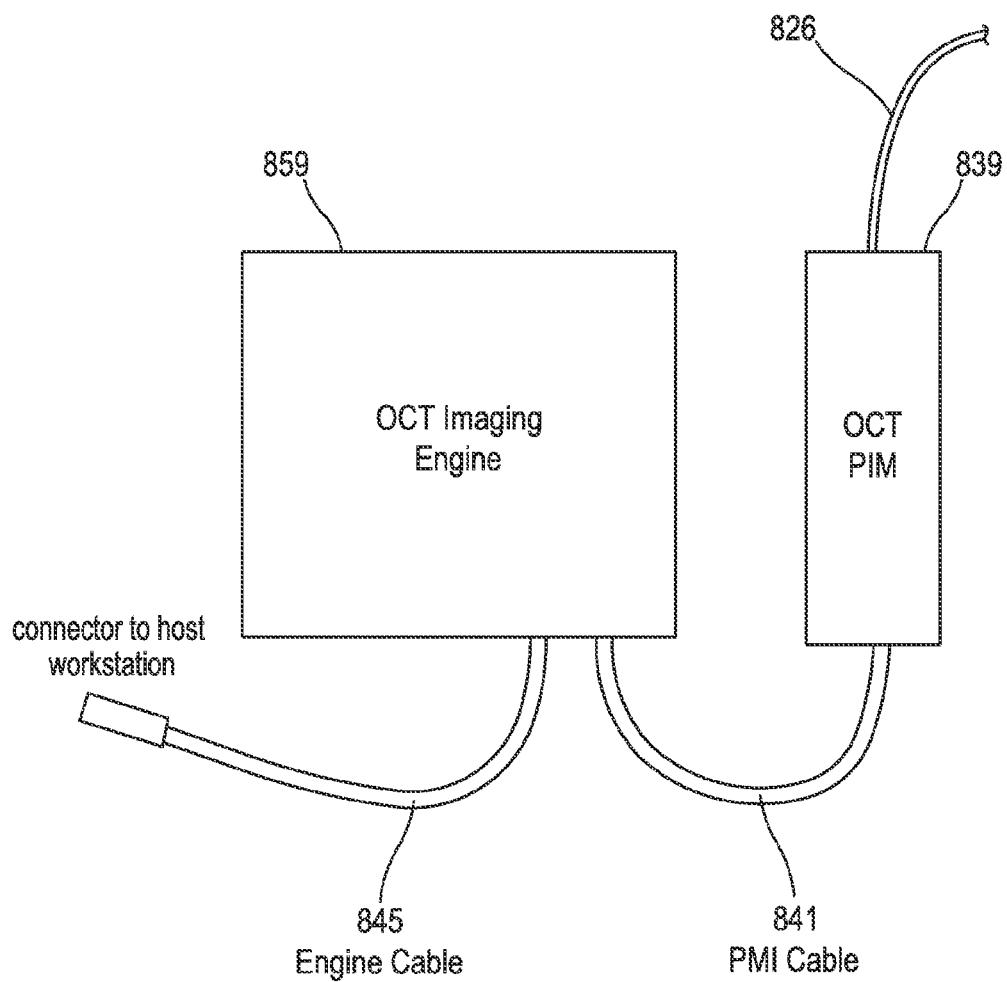
FIG. 3 is a diagram of components of an optical coherence tomography (OCT) system.

This invention generally relates to automatically detecting stents in intraluminal medical imaging. Medical imaging is a general technology class in which sectional and multidimensional anatomic images are constructed from acquired data. The data can be collected from a variety of signal acquisition systems including, but not limited to, magnetic resonance imaging (MRI), radiography methods including fluoroscopy, x-ray tomography, computed axial tomography and computed tomography, nuclear medicine techniques such as scintigraphy, positron emission tomography and single photon emission computed tomography, photo acoustic imaging ultrasound devices and methods including, but not limited to, intravascular ultrasound spectroscopy (IVUS), ultrasound modulated optical tomography, ultrasound transmission tomography, other tomographic techniques such as electrical capacitance, magnetic induction, functional MRI, optical projection and thermo-acoustic imaging, combinations thereof and combinations with other medical techniques that produce one-, two- and three-dimensional images. Although the exemplifications described herein are drawn to the invention as applied to OCT, at least all of these techniques are contemplated for use with the systems and methods of the present invention.

Systems and methods of the invention have application in intravascular imaging methodologies such as intravascular ultrasound (IVUS) and optical coherence tomography (OCT) among others that produce a three-dimensional image of a lumen. A segment of a lumen 101 is shown in FIG. 1 having a feature 113 of interest. FIG. 2 shows a cross-section of lumen 101 through feature 113. In certain embodiments, intravascular imaging involves positioning an imaging device near feature 113 and collecting data representing a three-dimensional image.

OCT is a medical imaging methodology using a specially designed catheter with a miniaturized near infrared light-emitting probe attached to the distal end of the catheter. As an optical signal acquisition and processing method, it captures micrometer-resolution, three-dimensional images from within optical scattering media (e.g., biological tissue). Commercially available OCT systems are employed in diverse applications, including art conservation and diagnostic medicine, notably in ophthalmology where it can be used to obtain detailed images from within the retina. The detailed images of the retina allow one to identify several eye diseases and eye trauma. Recently it has also begun to be used in interventional cardiology to help diagnose coronary artery disease. OCT allows the application of interferometric technology to see from inside, for example, blood vessels, visualizing the endothelium (inner wall) of blood vessels in living individuals.

Other applications of OCT and other signal processing imaging systems for biomedical imaging include use in: dermatology in order to image subsurface structural and blood flow formation; dentistry in order to image the structure of teeth and gum line to identify and track de-mineralization and re-mineralization, tarter, caries, and periodontal disease; gastroenterology in order to image the gastrointestinal tract to detect polyps and inflammation, such as that caused by Crohn's disease and ulcerative colitis; cancer diagnostics in order to discriminate between malignant and normal tissue.

Generally, an OCT system comprises three components which are 1) an imaging catheter 2) OCT imaging hardware, 3) host application software. When utilized, the components are capable of obtaining OCT data, processing OCT data, and transmitting captured data to a host system. OCT systems and methods are generally described in Milner et al., U.S. Patent Application Publication No. 2011/0152771, Condit et al., U.S. Patent Application Publication No. 2010/0220334, Castella et al., U.S. Patent Application Publication No. 2009/

0043191, Milner et al., U.S. Patent Application Publication No. 2008/0291463, and Kemp, N., U.S. Patent Application Publication No. 2008/0180683, the content of each of which is incorporated by reference in its entirety. In certain embodiments, systems and methods of the invention include processing hardware configured to interact with more than one different three dimensional imaging system so that the tissue imaging devices and methods described here in can be alternatively used with OCT, IVUS, or other hardware.

Various lumen of biological structures may be imaged with aforementioned imaging technologies in addition to blood vessels, including, but not limited, to vasculature of the lymphatic and nervous systems, various structures of the gastrointestinal tract including lumen of the small intestine, large intestine, stomach, esophagus, colon, pancreatic duct, bile duct, hepatic duct, lumen of the reproductive tract including the vas deferens, vagina, uterus and fallopian tubes, structures of the urinary tract including urinary collecting ducts, renal tubules, ureter, and bladder, and structures of the head and neck and pulmonary system including sinuses, parotid, trachea, bronchi, and lungs.

The arteries of the heart are particularly useful to examine with imaging devices such as OCT. OCT imaging of the coronary arteries can determine the amount of plaque built up at any particular point in the coronary artery. The accumulation of plaque within the artery wall over decades is the setup for vulnerable plaque which, in turn, leads to heart attack and stenosis (narrowing) of the artery. OCT is useful in determining both plaque volume within the wall of the artery and/or the degree of stenosis of the artery lumen. It can be especially useful in situations in which angiographic imaging is considered unreliable, such as for the lumen of ostial lesions or where angiographic images do not visualize lumen segments adequately. Example regions include those with multiple overlapping arterial segments. It is also used to assess the effects of treatments of stenosis such as with hydraulic angioplasty expansion of the artery, with or without stents, and the results of medical therapy over time. In an exemplary embodiment, the invention provides a system for capturing a three dimensional image by OCT.

In OCT, a light source delivers a beam of light to an imaging device to image target tissue. Light sources can be broad spectrum light sources, pulsating light sources, continuous wave light sources, and include superluminescent diodes, ultrashort pulsed lasers and supercontinuum. Within the light source is an optical amplifier and a tunable filter that allows a user to select a wavelength of light to be amplified. Wavelengths commonly used in medical applications include near-infrared light, for example between about 800 nm and about 1700 nm.

Methods of the invention apply to image data obtained from obtained from any OCT system, including OCT systems that operate in either the time domain or frequency (high definition) domain. Basic differences between time-domain OCT and frequency-domain OCT is that in time-domain OCT, the scanning mechanism is a movable mirror, which is scanned as a function of time during the image acquisition. However, in the frequency-domain OCT, there are no moving parts and the image is scanned as a function of frequency or wavelength.

In time-domain OCT systems an interference spectrum is obtained by moving the scanning mechanism, such as a reference mirror, longitudinally to change the reference path and match multiple optical paths due to reflections within the sample. The signal giving the reflectivity is sampled over time, and light traveling at a specific distance creates interference in the detector. Moving the scanning mechanism laterally (or rotationally) across the sample produces two-dimensional and three-dimensional images.

In frequency domain OCT, a light source capable of emitting a range of optical frequencies excites an interferometer, the interferometer combines the light returned from a sample with a reference beam of light from the same source, and the intensity of the combined light is recorded as a function of optical frequency to form an interference spectrum. A Fourier transform of the interference spectrum provides the reflectance distribution along the depth within the sample.

Several methods of frequency domain OCT are described in the literature. In spectral-domain OCT (SD-OCT), also sometimes called "Spectral Radar" (Optics letters, Vol. 21, No. 14 (1996) 1087-1089), a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith, L. M. and C. C. Dobson, Applied Optics 28: 3339-3342), wherein the distance to a scatterer is determined by the wavelength dependent fringe spacing within the power spectrum. SD-OCT has enabled the determination of distance and scattering intensity of multiple scatters lying along the illumination axis by analyzing a single the exposure of an array of optical detectors so that no scanning in depth is necessary. Typically the light source emits a broad range of optical frequencies simultaneously. Alternatively, in swept-source OCT, the interference spectrum is recorded by using a source with adjustable optical frequency, with the optical frequency of the source swept through a range of optical frequencies, and recording the interfered light intensity as a function of time during the sweep. An example of swept-source OCT is described in U.S. Pat. No. 5,321,501.

Generally, time domain systems and frequency domain systems can further vary in type based upon the optical layout of the systems: common beam path systems and differential beam path systems. A common beam path system sends all produced light through a single optical fiber to generate a reference signal and a sample signal whereas a differential beam path system splits the produced light such that a portion of the light is directed to the sample and the other portion is directed to a reference surface. Common beam path systems are described in U.S. Pat. No. 7,999,938; U.S. Pat. No. 7,995,210; and U.S. Pat. No. 7,787,127 and differential beam path systems are described in U.S. Pat. No. 7,783,337; U.S. Pat. No. 6,134,003; and U.S. Pat. No. 6,421,164, the contents of each of which are incorporated by reference herein in its entirety.

In certain embodiments, the invention provides a differential beam path OCT system with intravascular imaging capability as illustrated in FIG. 3. For intravascular imaging, a light beam is delivered to the vessel lumen via a fiber-optic based imaging catheter 826. The imaging catheter is connected through hardware to software on a host workstation. The hardware includes an imagining engine 859 and a hand-held patient interface module (PIM) 839 that includes user controls. The proximal end of the imaging catheter is connected to PIM 839, which is connected to an imaging engine as shown in FIG. 3.

Figure 4:
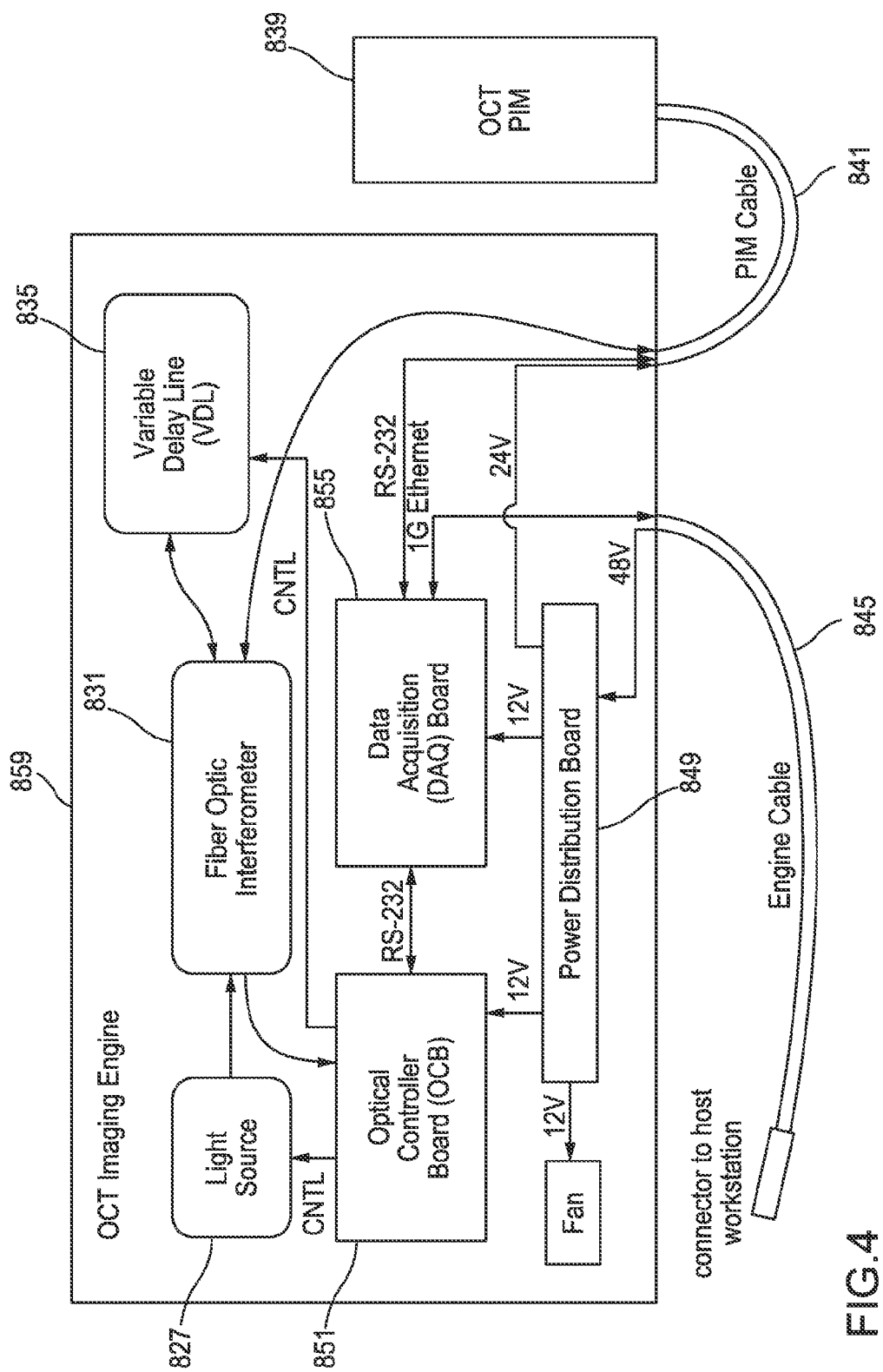
FIG. 4 is a diagram of the imaging engine shown in FIG. 3.

As shown in FIG. 4, the imaging engine 859 (e.g., a bedside unit) houses a power supply 849, light source 827, interferometer 831, and variable delay line 835 as well as a data acquisition (DAQ) board 855 and optical controller board (OCB) 851. A PIM cable 841 connects the imagine engine

859 to the PIM 839 and an engine cable 845 connects the imaging engine 859 to the host workstation.

Figure 5:
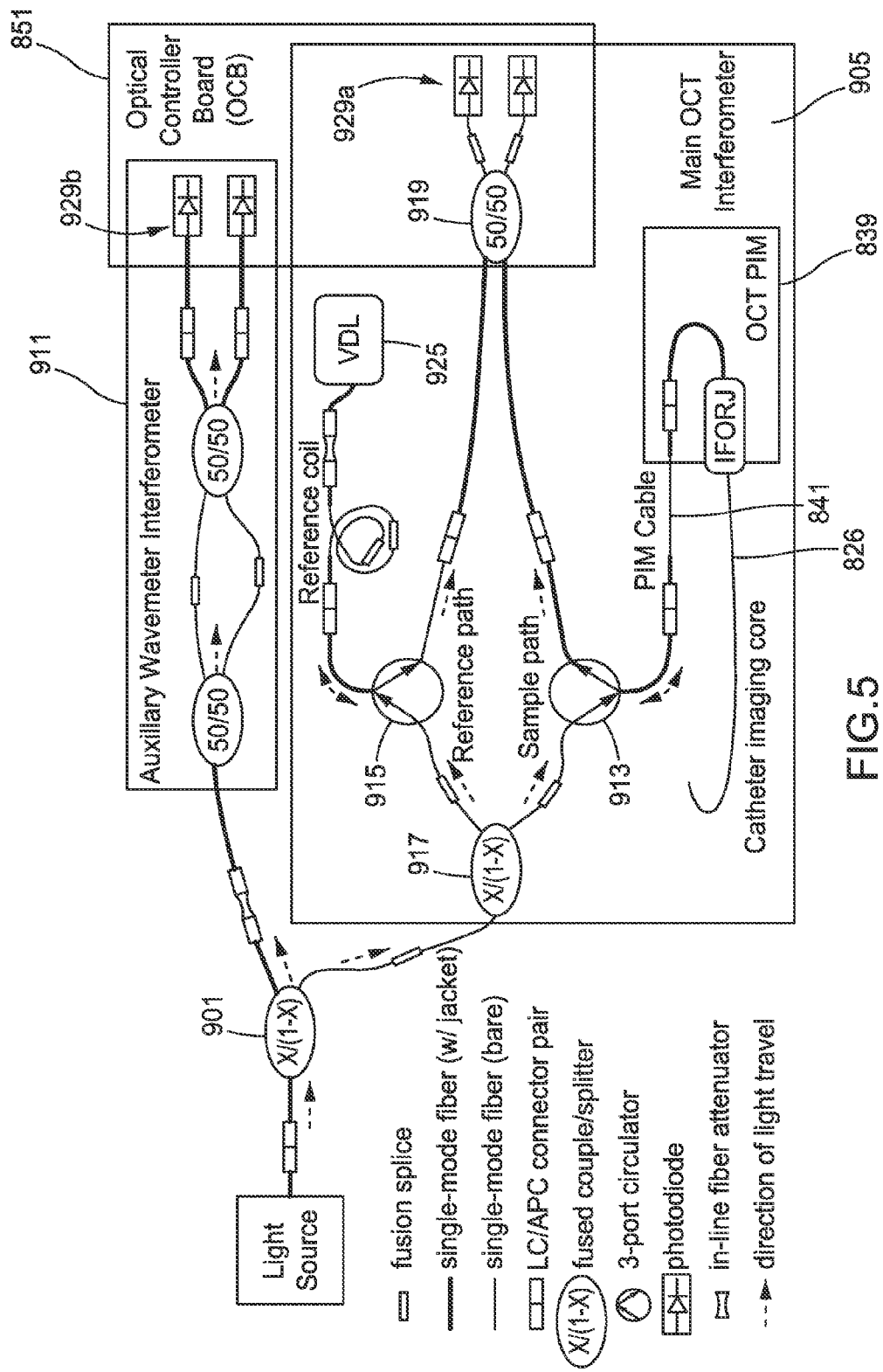
FIG. 5 is a diagram of a light path in an OCT system of certain embodiments of the invention.

FIG. 5 shows light path in a differential beam path system according to an exemplary embodiment of the invention. Light for image capture originates within the light source 827. This light is split between an OCT interferometer 905 and an auxiliary, or "clock", interferometer 911. Light directed to the OCT interferometer is further split by splitter 917 and recombined by splitter 919 with an asymmetric split ratio. The majority of the light is guided into the sample path 913 and the remainder into a reference path 915. The sample path includes optical fibers running through the PIM 839 and the imaging catheter 826 and terminating at the distal end of the imaging catheter where the image is captured.

Typical intravascular OCT involves introducing the imaging catheter into a patient's target vessel using standard interventional techniques and tools such as a guide wire, guide catheter, and angiography system. The imaging catheter may be integrated with IVUS by an OCT-IVUS system for concurrent imaging, as described in, for example, Castella et al. U.S. Patent Application Publication No. 2009/0043191 and Dick et al. U.S. Patent Application Publication No. 2009/0018393, both incorporated by reference in their entirety herein.

Figure 6:
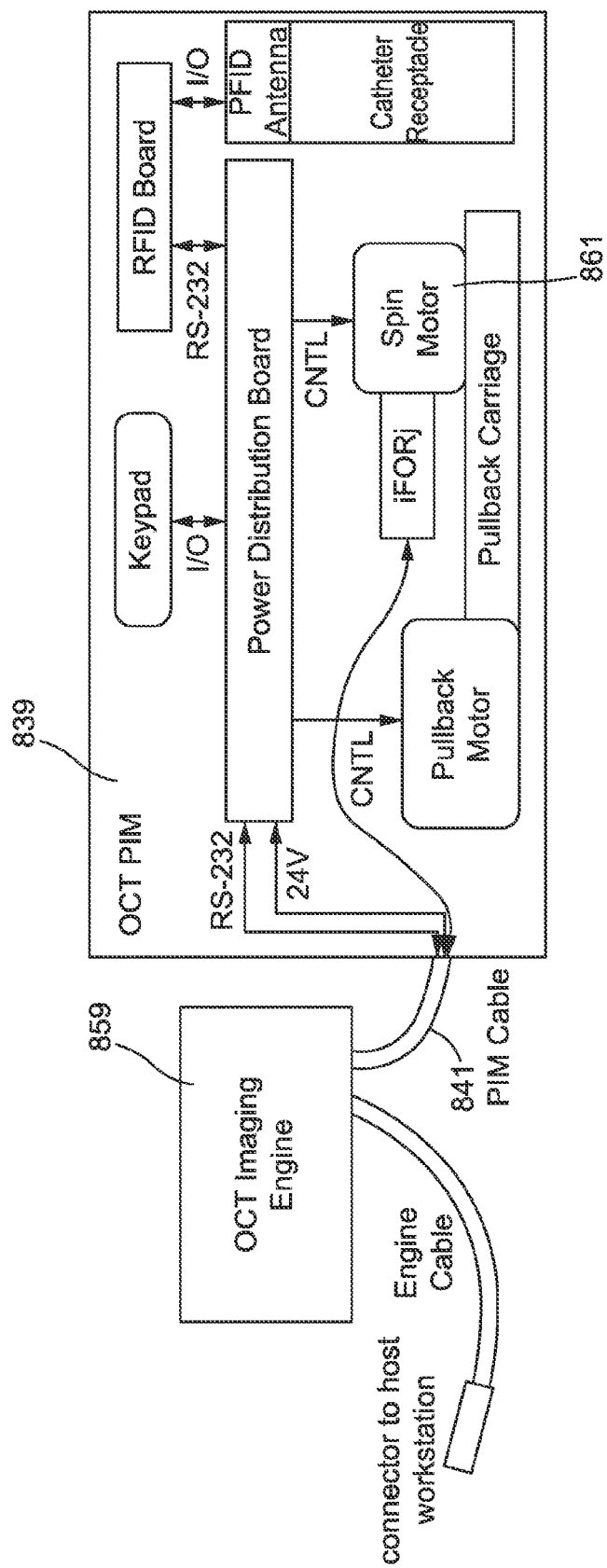
FIG. 6 is a patient interface module of an OCT system.
Figure 7:
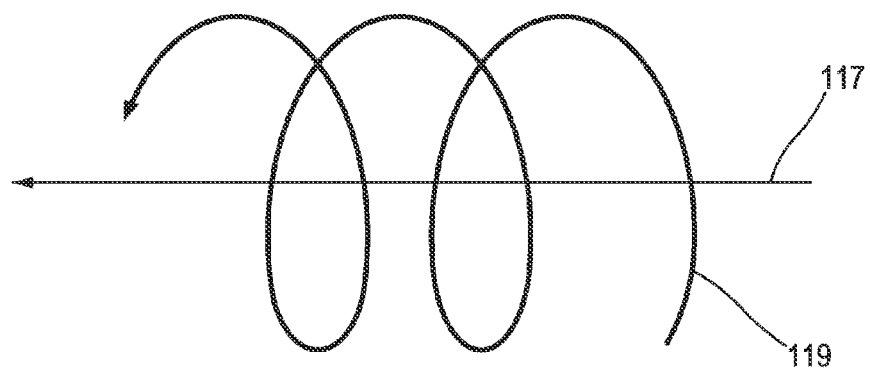
FIG. 7 is an illustration of the motion of parts of an imaging catheter according to certain embodiments of the invention.
Figure 8:
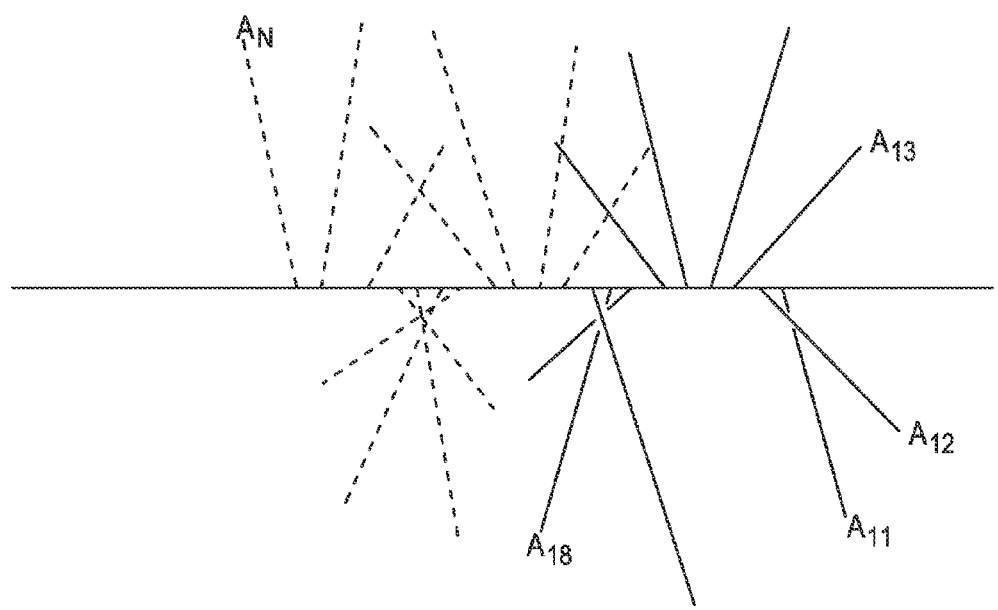
FIG. 8 shows an array of A scan lines of a three-dimensional imaging system according to certain embodiments of the invention.

Rotation of the imaging catheter is driven by spin motor 861 while translation is driven by pullback motor 865, shown in FIG. 6. This results in a motion for image capture described by FIG. 7. Blood in the vessel is temporarily flushed with a clear solution for imaging. When operation is triggered from the PIM or control console, the imaging core of the catheter rotates while collecting image data. Using light provided by the imaging engine, the inner core sends light into the tissue in an array of A-scan lines as illustrated in FIG. 8 and detects reflected light.

Figure 9:
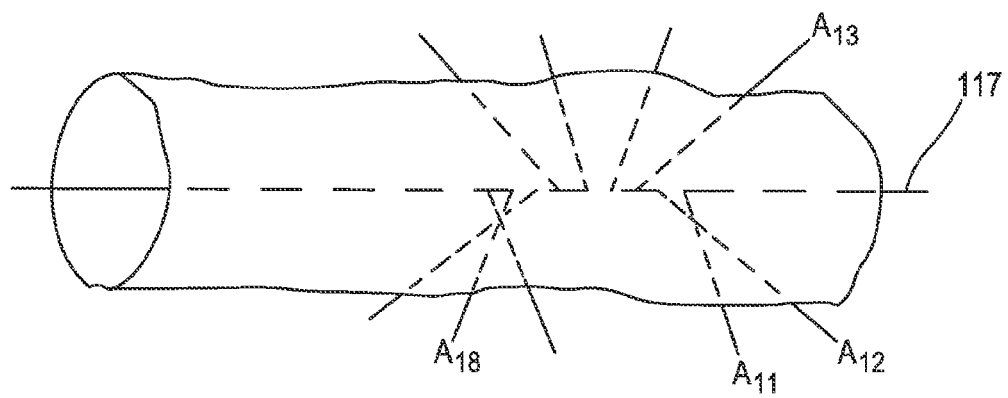
FIG. 9 shows the positioning of A scans with in a vessel.

FIG. 9 shows the positioning of A-scans within a vessel. Each place where one of A-scans A11, A12, . . . , AN intersects a surface of a feature within vessel 101 (e.g., a vessel wall) coherent light is reflected and detected. Catheter 826 translates along axis 117 being pushed or pulled by pullback motor 865.

The reflected, detected light is transmitted along sample path 913 to be recombined with the light from reference path 915 at splitter 919 (FIG. 5). A variable delay line (VDL) 925 on the reference path uses an adjustable fiber coil to match the length of reference path 915 to the length of sample path 913. The reference path length is adjusted by a stepper motor translating a mirror on a translation stage under the control of firmware or software. The free-space optical beam on the inside of the VDL 925 experiences more delay as the mirror moves away from the fixed input/output fiber.

The combined light from splitter 919 is split into orthogonal polarization states, resulting in RF-band polarization-diverse temporal interference fringe signals. The interference fringe signals are converted to photocurrents using PIN photodiodes 929*a*, 929*b*, . . . on the OCB 851 as shown in FIG. 5. The interfering, polarization splitting, and detection steps are done by a polarization diversity module (PDM) on the OCB. Signal from the OCB is sent to the DAQ 855, shown in FIG. 4. The DAQ includes a digital signal processing (DSP) microprocessor and a field programmable gate array (FPGA) to digitize signals and communicate with the host workstation and the PIM. The FPGA converts raw optical interference signals into meaningful OCT images. The DAQ also compresses data as necessary to reduce image transfer bandwidth to 1 Gbps (e.g., compressing frames with a glossy compression JPEG encoder).

Data is collected from A-scans A11, A12, . . . , AN and stored in a tangible, non-transitory memory. Typically, rotational systems consist of an imaging core which rotates and pulls back (or pushes forward) while recording an image video loop. This motion results in a three dimensional dataset of two dimensional image frames, where each frame provides a 360° slice of the vessel at different longitudinal locations.

Figure 10:
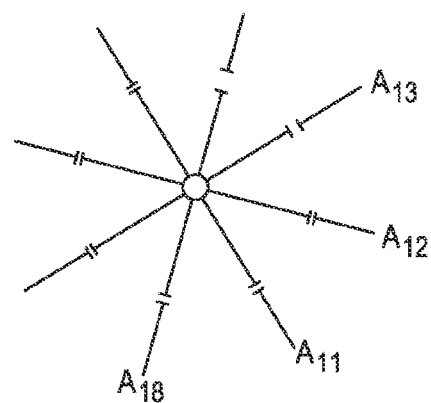
FIG. 10 illustrates a set of A scans used to compose a B scan according to certain embodiments of the invention.

A set of A-scans generally corresponding to one rotation of catheter 826 around axis 117 collectively define a B-scan. FIG. 10 illustrates a set of A-scans A11, A12, . . . , A18 used to compose a B-scan according to certain embodiments of the invention. These A-scan lines are shown as would be seen looking down axis 117 (i.e., longitudinal distance between then is not shown). While eight A-scan lines are illustrated in FIG. 10, typical OCT applications can include between 300 and 1,000 A-scan lines to create a B-scan (e.g., about 660). Reflections detected along each A-scan line are associated with features within the imaged tissue. Reflected light from each A-scan is combined with corresponding light that was split and sent through reference path 915 and VDL 925 and interference between these two light paths as they are recombined indicates features in the tissue.

Figure 11:
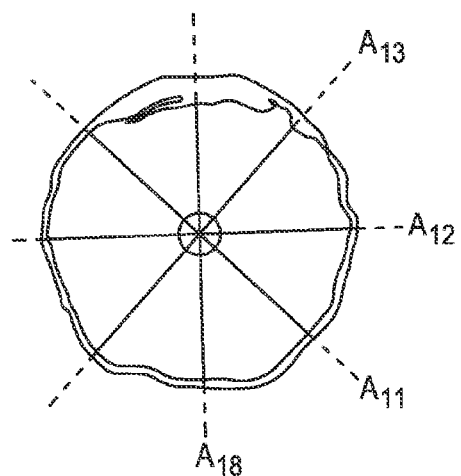
FIG. 11 shows the set of A scans shown in FIG. 10 within a cross section of a vessel.
Figure 12:
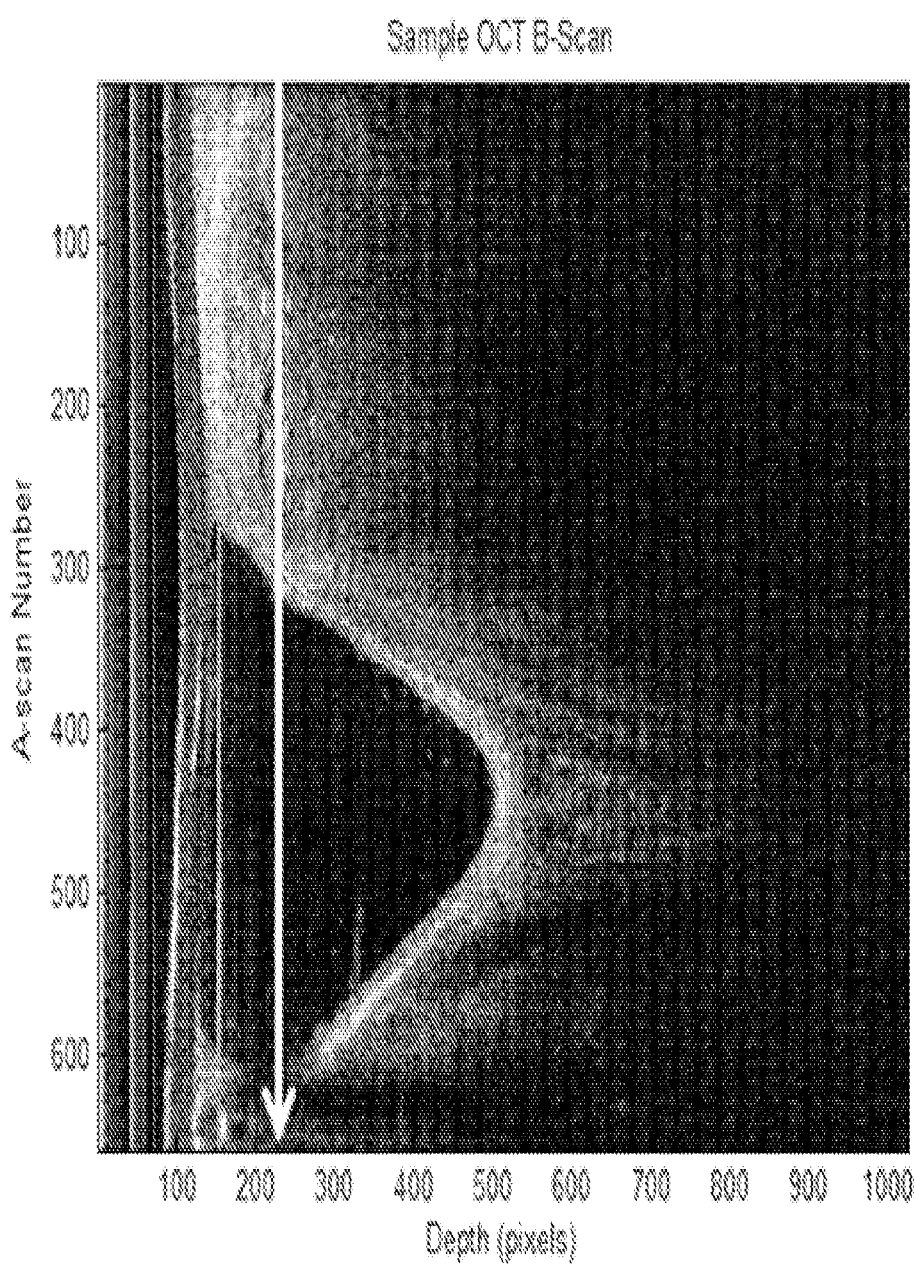
FIG. 12 shows a sample OCT B-Scan image calculated from 660 A-scans.
Figure 13:
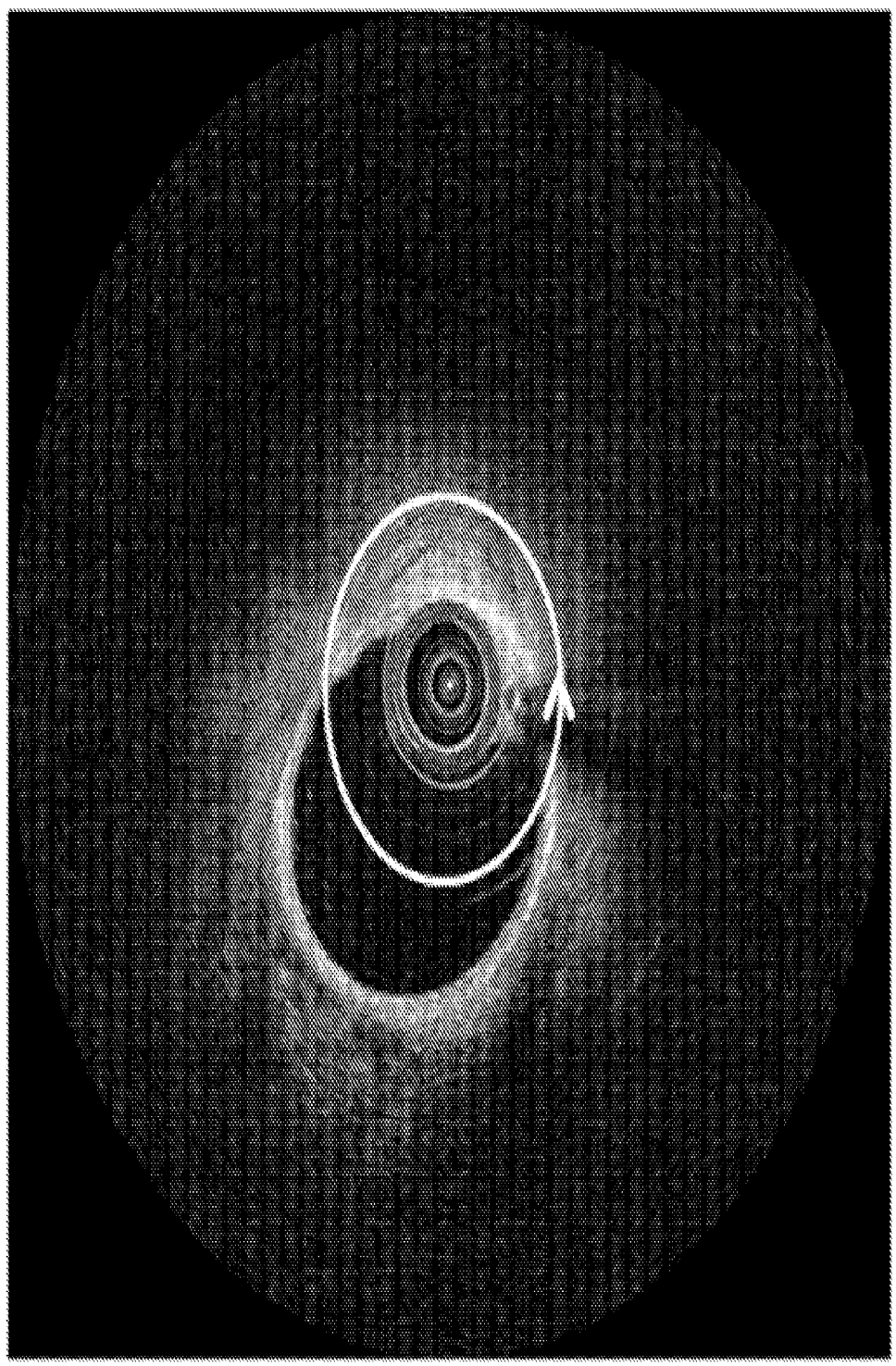
FIG. 13 shows a scan-converted OCT image from the B-scan of FIG. 12.

The data of all the A-scan lines together represent a three-dimensional image of the tissue. The data of the A-scan lines generally referred to as a B-scan can be used to create an image of a cross section of the tissue, sometimes referred to as a tomographic view. For example, FIG. 11 shows the set of A-scans shown in FIG. 10 within a cross section of a vessel. The set of A-scans obtained by rotational imaging modality can be combined to form a B-scan. FIG. 12 is an example of an OCT polar coordinate B-Scan with 660 A-scans. To create a final tomographic view of the vessel, the B-scan is scan converted to a Cartesian coordinate system. FIG. 13 displays the scan-converted image of the B-scan in FIG. 12.

Systems and methods of the invention include image-processing techniques that provide automatic detection of objects, such as stents, within intraluminal images. Typically, the OCT intraluminal image is an intravascular image taken within a lumen of a blood vessel, but the detection methods described herein can be used to detect objects within other biological lumens, such as the intestine. Although the following description is directed towards detecting objects in OCT images, one skilled in the art would readily recognize that methods and systems of intention can be utilized to detect objects in any intraluminal images obtained from any other imaging technique, such as intravascular ultrasound imaging (IVUS) and combined OCT-IVUS.

Embodiments of the invention provide for algorithms to detect a stents location within the polar coordinate system using features within one-dimensional images, such as A-scan, two-dimensional images, such as a B-scan, and/or three-dimensional images. Once the polar coordinates of the object are detected, the polar coordinates can be converted to the Cartesian coordinates and displayed as a tomographic image. Thus, a three-dimensional profile of the stent can be detected and displayed to a user. In addition, with the polar coordinates of the stent automatically detected, the strent stut apposition or coverage relative to the lumen border can easily be computed. Additionally, these algorithms can be applied to pre-scan converted data and to scan converted data.

Because the algorithms disclosed herein can be applied to every frame taken during an OCT imaging run, the location of the object can be detected in one or more frames can be computed and provided to the user on a graphic display.

The 1-D, 2-D or 3-D images include data, such as pixel data, which includes pixel locations, pixel intensity, color intensities, which includes the RGB color channel for the pixels, and/or volumetric data, which includes the x, y, z coordinates. The data obtained from the image are considered features within the image that can be used to classify or detect the object. Images can be associated with other data features such as amplitude, phase, frequency, polarity, velocity, weight, density, transparency, reflectance, hardness, and temperature.

Figure 14:
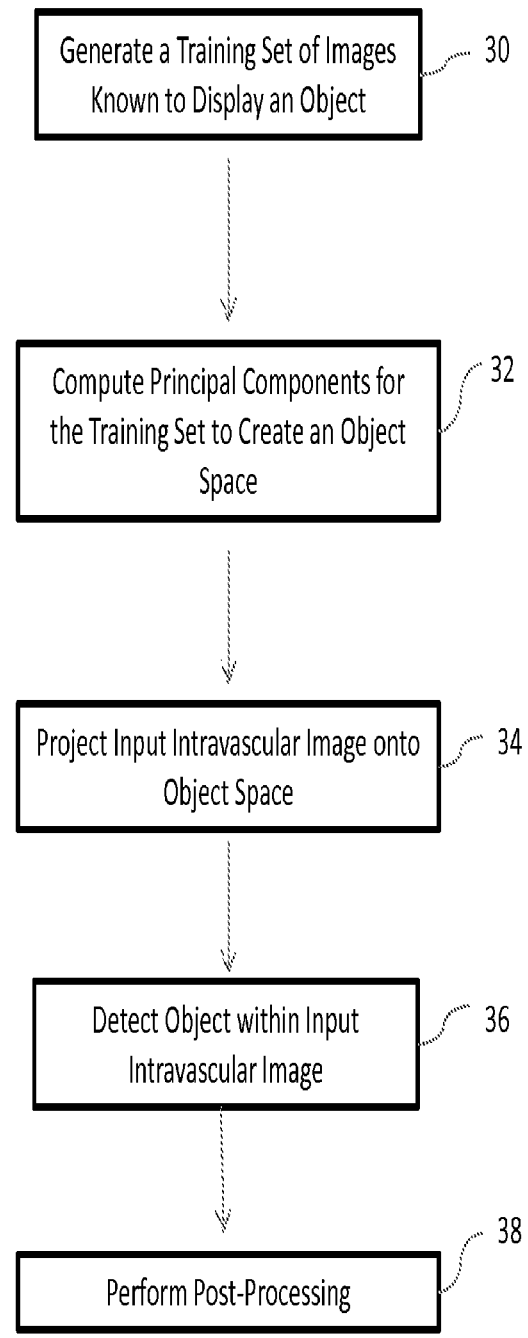
FIG. 14 depicts a basic flow chart for principal component analysis for stent detection.

FIG. 14 exemplifies the steps employed in an embodiment for detecting stents using an adaptation of principal component analysis, a known signal processing approach. Exemplary principal components analysis techniques can be found in M. Turk and A. Pentland "Eigenfaces for Recognition" and Pentland et al. "View-based and modular eigenspaces for face recognition" in Proc. IEEE Conf. Comput Vision. @ Pattern Recogn. These techniques have been adapted to of detection of object in intraluminal images. The first step 30 includes generating a training set of pre-defined intraluminal images for an object. The second step 32 involves computing the principal components for the object to create an object space. The third step 34 involves projecting an input intraluminal image onto the object space. The fourth step 36 involves detecting the object within the intraluminal image. Methods of the invention are not limited to stent detection, but can be used to detect any object within an intraluminal image, such as guidewire, lumen border, and tissue.

The first step 30 is to generate a training set of pre-defined intraluminal images known to contain an object so that the images can be used to train the processor to identify the object within images or regions of images not known to contain the object. Images known to contain the object include images in which the object was manually located and detected. The images known to contain the object can be obtained online or compiled off-line. In certain aspects, the training set of pre-defined intraluminal images can be pre-processed by, for example filtering the images prior to generating a training set.

In certain aspects, the images for the training set are all the same size or interpolated to the same size. Data, such as pixel intensity, can be arranged into a matrix for principal component analysis. In one aspect, data from each image in the training set can be taken and stacked into a matrix, wherein each column in the matrix represents a different image and each row within a column of the matrix represents the same pixel location in each training image. The rows can be through of as features and each column is a sample of that feature.

It should be noted that in all training sets generated for use in the embodiments described herein are not limited to a fixed amount of pre-defined images. Rather, the training sets can be made to have an adaptive training process. For example, by continually updating training sets with input intraluminal images that have been positively identified for a specific object. As the training set database grows, so does the accuracy of the detection.

Once a matrix for the training set of pre-defined matrix is compiled, the principal components for the training set matrix are computed to create an object space, as in the second step 32. The principal components can be computed by directly computing the eigenvectors of a covariance matrix computed from the training data set matrix or by utilizing Singular Value Decomposition (SVD) of the training set data matrix, which is described in detail in, for example, Abdi, H, & Williams, L. J. (2010). "Principal component analysis." *Wiley Interdisciplinary Reviews: Computational Statistics*, 2: 433-459. By calculating the principal components, one can determine which vectors out of the set of pre-defined images best account for the distribution of object images within the entire object space. Therefore, only the top n eigenvectors are kept in order to create a basis which accounts for most of the variance within the image set. These vectors define the subspace of object images, and constitute the object space. The principal components are stored within a memory and utilized later on to detect an object within input intraluminal images.

In order to utilize the principal components to detect object in unknown input images, a threshold error can be computed. In one aspect, the threshold value is computed by determining the amount of error between one or more of pre-defined images known to contain the object and the object space. This threshold error can be obtained using the same pre-defined images that were used to create the object space or another image known to create the same object. In order to determine error, a pre-defined image can be projected onto the object space in order to determine the distance between points in the pre-defined image in comparison to the object space. In certain aspects, the error is the Euclidean distance between the training set image and the object space. This error computation can be repeated for each pre-defined image in the training set, a portion of pre-defined images in the training set, or for multiple pre-defined images outside of the training set.

Using the computed errors, one can calculate a threshold error value that can be used to determine if an unknown image contains the object. For example, unknown images that are projected against the object space that have an error greater than the threshold error will not be determined to contain the object and unknown images with an error smaller than the threshold error will return a positive detection for the object. The threshold error can be the maximum error, minimum error, or an average computation of the error, such as the quadratic mean, arithmetic mean, mode, medium, or any other statistical average known in the art.

The third step 34 involves projecting an input intraluminal image onto the object space. The input intraluminal image can be an image taken during an OCT procedure in real-time or a previously taken image, for example, an image that was stored or uploaded onto the computing system. The error between the input intraluminal image and the object space is computed in a similar manner the error was computed for each pre-defined image to determine a threshold error. In some embodiments, the error is the Euclidean distance between the input image and the object space. After the error is computed, the error of the input intraluminal image can be used to detect the object, as in the fourth step 36. For example, if the error is below a threshold value, the object is positively detected in the input intraluminal image. If the error is above the threshold image, then the object is negatively detected within input intraluminal image.

In certain aspects, an object space is created for two or more objects in order to compare the input intraluminal image to two or more object spaces. Step 30 and step 32 are repeated for at least one other object. In one embodiment, a training set is generated of pre-defined intraluminal images known to contain stents and a training set is generated of pre-defined intraluminal images known to contain tissue, for example, imaging of a blood vessel without stents. The principal components are generated for both training sets to compute a tissue space and a stent space. For step 36, an input intraluminal image can be projected onto both the tissue space and the stent space, and a tissue error and a stent error can be calculated by comparing the input intraluminal image to both spaces. The set of principal components, tissue or stent, which most accurately represents the original image, is selected as the class matching the input intraluminal image, and the corresponding object is positively detected. For example, if the error between the stent and the input intraluminal image is less than the error between the tissue and the input intraluminal image, the stent is positively detected within the input intraluminal image.

In addition, a threshold error value can also be computed for each of the plurality of object spaces. A comparison between the input intraluminal image and each object space's threshold value can determine whether or not the object is present in the input intraluminal image. If the error is significantly high for both classes, this can indicate that the input intraluminal image does not match any of the data that was used in the training set. Comparing threshold error reduces the risk of misclassification when comparing simply comparing the magnitudes of the error. If the input intraluminal image does not match any of the training sets, an indicator can appear on an OCT graphical display to indicate to the user that manual detection may be required with respect to the unclassified input intraluminal image.

In a specific embodiment, method of FIG. 14 is adapted to train the classifier to detect tissue, stents, and guidewires. Guidewires are often misclassified as a stent strut because its features appear stent like in the intraluminal images. This prevents the likelihood that a positive detection for a stent is actually a guidewire.

In some embodiments, the input intraluminal image may be defined using the lumen border. In order to improve performance, the detected lumen border can be used to identify search regions for the object, such as a stent strut, within the image. In this aspect, the training sets of pre-defined images generated for an object will also be defined by the lumen border. For example, if a lumen border is detected within a region around +30 pixels, −200 pixels within an A-line, a training set can be formed using only the lumen border region of pre-defined images and an object space for that region can be generated. The same region of the A-line intraluminal image can be projected onto the object space to detect the object in that region. Detection occurs using the same error methods as previously described. The lumen border can be automatically or semi-automatically detected in an image using any method known in the art, such as the techniques disclosed in U.S. Pat. No. 7,978,916, S. Tanimoto, G. Rodriguez-Granillo, P. Barlis, S. de Winter, N. Bruining, R. Hamers, M. Knappen, S. Verheye, P. W. Serruys, and E. Regar, "A novel approach for quantitative analysis of intracoronary optical coherencetomography: High inter-observer agreement with computer-assisted contour detection," Cathet. Cardiovasc. Intervent. 72, 228-235 (2008); K. Sihan, C. Botka, F. Post, S. de Winter, E. Regar, R. Hamers, and N. Bruining, "A novel approach to quantitative analysis of intraluminal optical coherence tomography imaging," Comput. Cardiol. 1089-1092 (2008); J. Canny, "A computational approach to edge detection," IEEE Trans. Pattern Anal. Mach. Intell. 8, 679-698 (1986).

Additionally, methods of the invention provide for a post-processing step to, for example, detect the location of the stent within the image, for example, the stent depth. Any method known in the art can be used to locate the depth position of the stent, such as peak detection within some maximum distance of the detected lumen border can be used to identify the final location of the stent. Post-processing can be used to verify the detection of the stent within the image. For example, methods of the invention can also be combined with other algorithms or methods used to detect guidewires or other false stent detections. In one aspect, after detection of stents using the methods of the invention, a guidewire detection/tracking algorithm can be applied to the image to remove the false stent detections. Post-processing can also be used to visually illustrate the resulting stent detections within the intravascular image on a graphical user interface. For example, detected portions of the stent can be highlighted with a bolded line or circled within the image.

Figure 15:
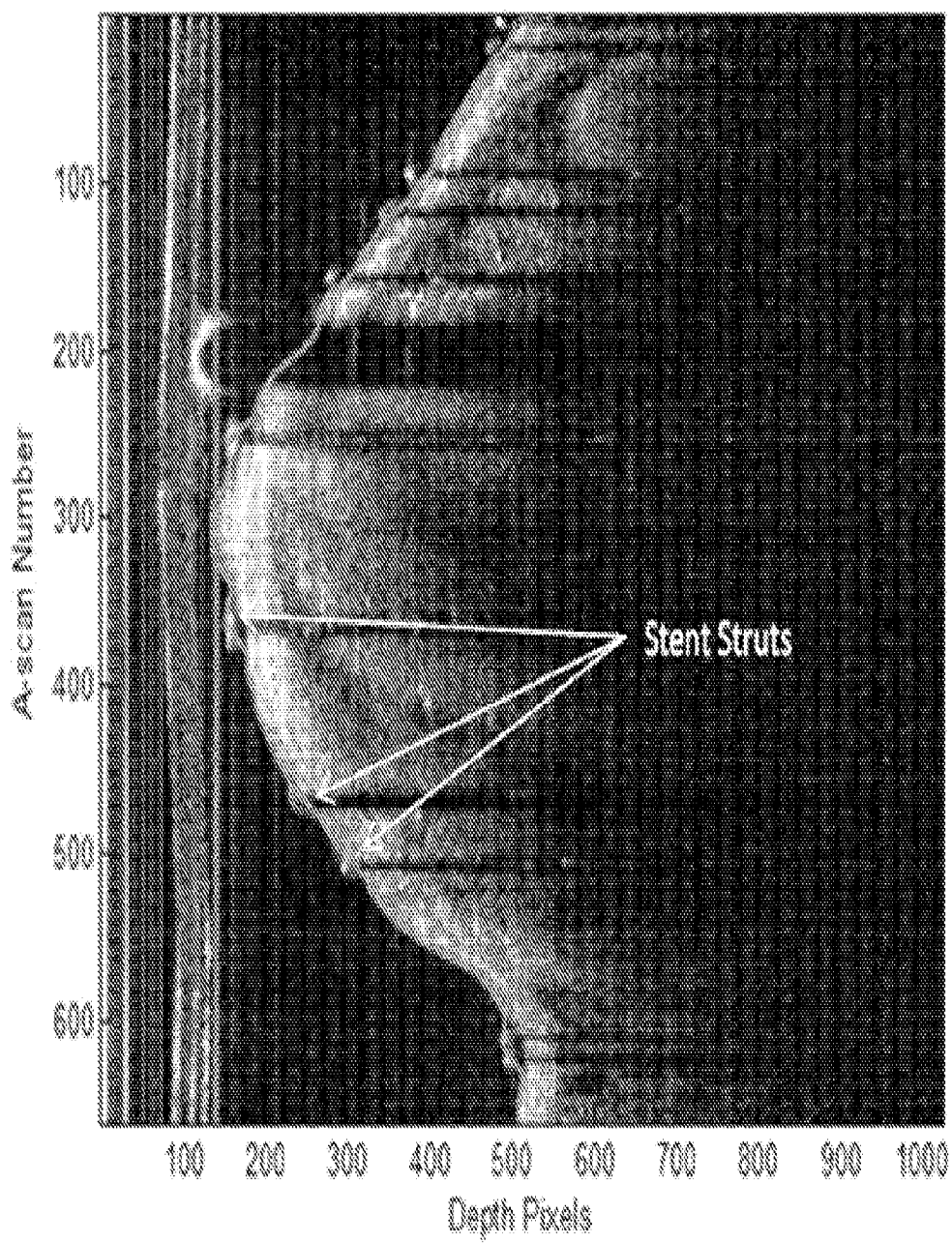
FIG. 15 depicts an example OCT B-Scan with stent struts detected following the principal component analysis outlined in FIG. 14.
Figure 17:
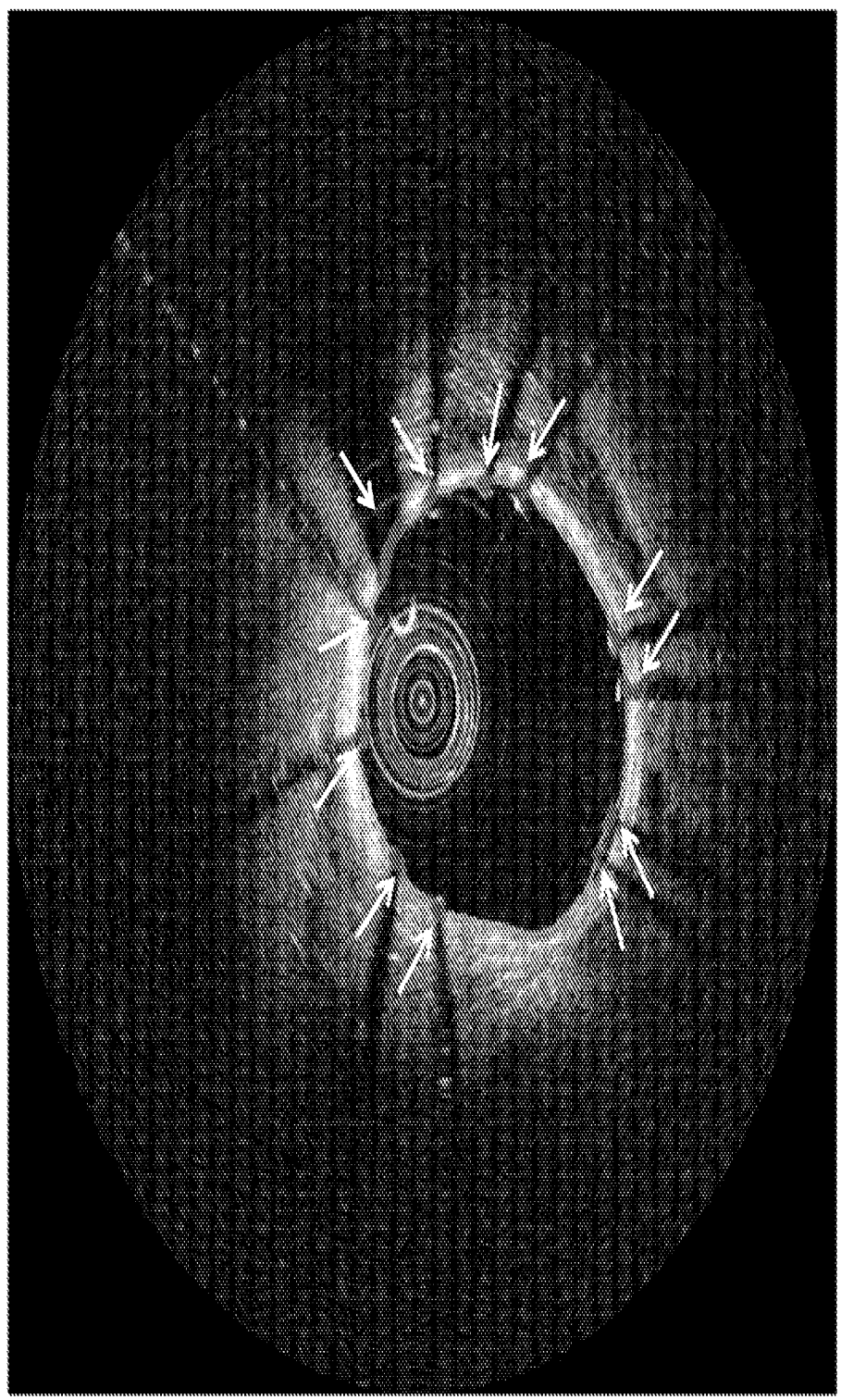
FIG. 17 depicts the resulting stent detections in scan-converted image of FIG. 15.
Figure 18:
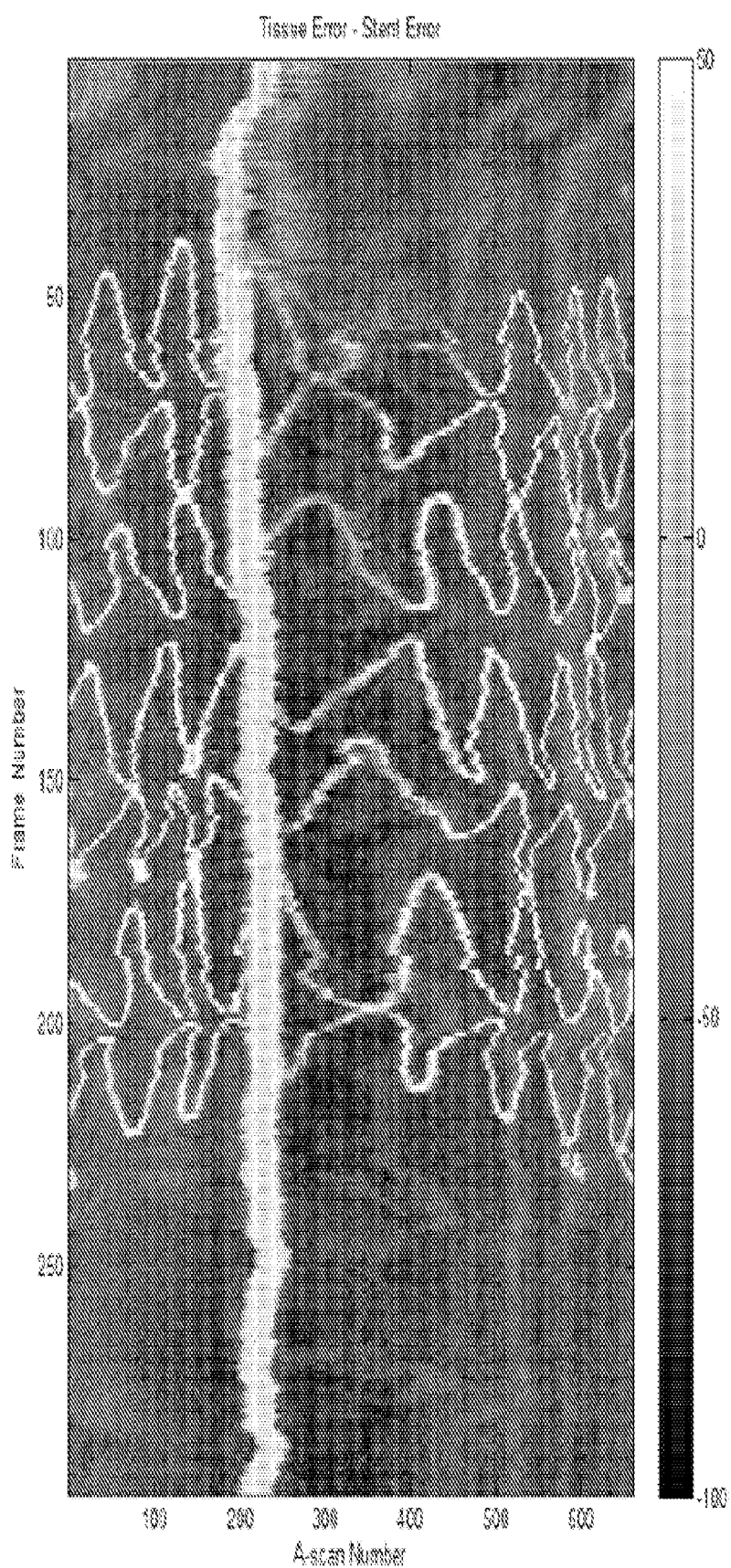
FIG. 18 depicts the tissue error and stent error from FIG. 16 for all frames in a pullback.
Figure 19:
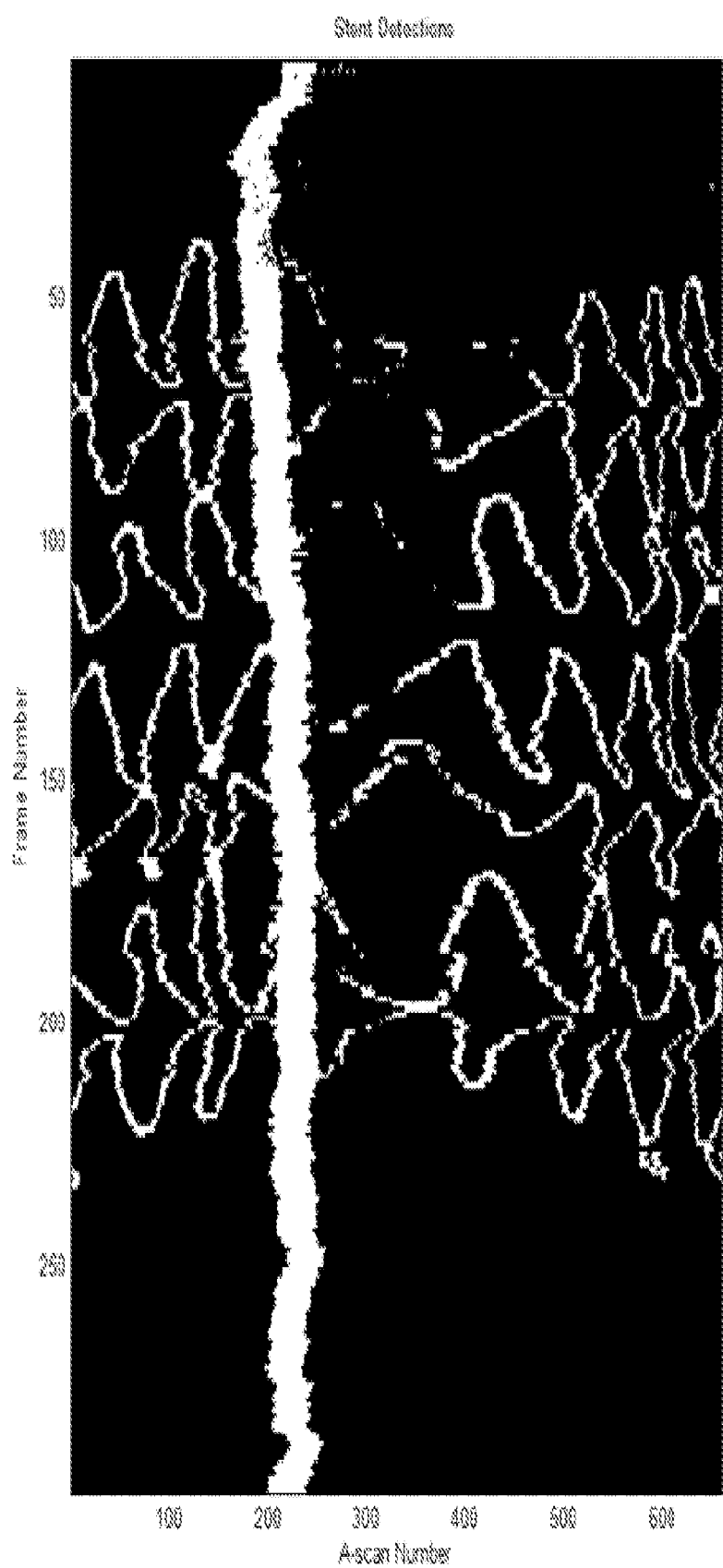
FIG. 19 depicts the corresponding stent detections from for all frames in a pullback.

The following description and figures illustrate stent detection following the block diagram in FIG. 14. FIG. 15 depicts an example of an OCT B-scan highlighting both detected stent struts and the automatically detected lumen border. A training set for stents and tissue were generated defined by the lumen border and a tissue space and stent space were computed. The A-line input intraluminal image around the border was projected onto a stent space and a tissue space. The error between the input intraluminal image and both the tissue space and stent space were computed, and plotted in FIG. 16. As shown in FIG. 16, the stent error is smaller at the location of the stents and the tissue error is higher at the locations of the stents. The difference between the stent error and the tissue error is also plotted in FIG. 16. Locations along the lumen border where the stent error is lower than the tissue error are classified as stents, and thus a stent is positively detected within the image. FIG. 17 displays the corresponding scan-converted image of the B-scan shown in FIG. 15. Post-processing was utilized to highlight the stent detections within the scan-converted image. The difference between the stent and tissue error for all frames in a pullback is plotted in a 2D splayed map in FIG. 18. The corresponding stent detections for all frames in this pull-back are provided in FIG. 19.

In another embodiment, objects are detected within an intraluminal image using region covariance descriptors to detect objects in images or in regions of images. This approach can be adapted to both 1D, 2D, and 3D intraluminal images. Similar to the detection method outlined in FIG. 13, this algorithm requires generating a training step of pre-defined intraluminal images and determining a compute for the training set that is compared to an input intraluminal image for detection. Regional covariance imaging techniques are known in the art and are described in, for example, Tuzel et al. "Region Covariance: A Fast Descriptor for Detection and Classification," European Conference on Computer Vision (ECCV), May 2006; Forstner and Moonen, "A metric for covariance matrices," Technical Report, Dept. of Geodesy and Geoinformatics, Stuttgart University (1999).

To detect stents or objects within intraluminal images using regional covariance, the first step is to generate a training set of pre-defined intraluminal images known to contain an object, for example, stent, tissue, or guidewire. A feature matrix can then be generated for the training set using a number of features within each pre-defined intraluminal image of the training set, e.g., the x and y coordinates of the pixel location, intensity of each pixel, and the first and second order derivatives of the image in the x and y direction. These features are computes for each pre-defined image within the training set. A pre-defined image of the training set can be any size image of m×n, and in one aspect m and n correspond to a dimension that is slightly larger than the width of a stent and the depth of tissue in an intraluminal image, and all images of the training set should be the same size. Although it is possible to perform regional covariance analysis on the entire image, use of m×n regions allows for targeted search of stents and other objects located on the lumen border. For example, the m×n image region can be created around the lumen border detected within an input intraluminal image, using any method of detecting the lumen border known in the art and discussed above.

Each pixel of a pre-defined intraluminal image is converted in to a feature matrix, using the equation listed below.

Equation 1: Feature Matrix
for Region Covariance Tracking [1]

$$F(x, y) = \left[ \left| x \; y \; I(x, y) \right. \right.$$

$$\left. \left| \frac{\partial I(x, y)}{\partial x} \right| \left| \frac{\partial I(x, y)}{\partial y} \right| \left| \frac{\partial^2 I(x, y)}{\partial x^2} \right| \left| \frac{\partial^2 I(x, y)}{\partial y^2} \right| \right]$$

Equation 1

In the above equation, x and y are indices and I is the intensity. For purposes of stent detection, the feature equation can be adapted to have more or less features or contain additional feature data, for example, the addition of RGB color values. Each input intraluminal image within the training set will have the same (x, y) pixel locations, and although not distinguishing, these coordinates are useful to correlate other features that vary from image to image. Once the feature matrix is computed, a covariance matrix for the set of features for each image can be computed using the following equation, where z represents the features, u is the mean of the feature samples, and T is a transpose operator.

$$C_R = \frac{1}{n-1} \sum_{k=1}^{n} (z_k - \mu)(z_k - \mu)^T$$

Equation 2

The above process is repeated for each pre-defined intraluminal image within the training set, and the covariance matrices are saved in the memory for later use during detection of objects of unknown input intraluminal images. The covariance matrices represent subspaces of the object.

In order to detect an object in the input intraluminal image, the input intraluminal image is broken down into the same m×n regions as the pre-defined images of the training set to identify, for example, stent locations. The covariance matrix of the input intraluminal image for the region is computed and compared to each covariance matrix of the training set. The comparison of the covariance matrix involves performing a distance calculation, or error calculation, between feature points within the covariance matrices. Any method known in the art for calculating the distance between covariance matrices can be used or adapted to calculate the distance between the unknown input intraluminal image covariance matrix and the covariance matrices of the pre-defined training. See for example, J. N. L. Brümmer and L. R. Strydom, "An euclidean distance measure between covariance matrices of speechcepstra for text-independent speaker recognition," in Proc. 1997 South African Symp. Communications and Signal Processing, 1997, pp. 167-172; W. Förstner and B. Moonen, A Metric for Covariance Matrices Dept. Geodesy and Geoinformatics, Stuttgart Univ., Stuttgart, Germany, 1999; Ö Tüzel, F. Porikli, and P. Meer, "Region covariance: A fast descriptor and for detection and classification," in Proc. Image and Vision Computing, Auckland, New Zealand, 2004.

A threshold error can be determined for the training set and used to determine whether the distance between the input intraluminal image and training set images are indicative of a positive detection of the object. Any method can be used to create a threshold distance. For example, the threshold distance is obtained by calculating the covariance distance between the training set images and selecting the maximum distance as a threshold distance, or calculating an average value as a threshold distance.

Like previous embodiments, the regional covariance approach can also be used to detect one or more objects within an input intravascular image by generating covariance matrices for more than one object. For example, a training set of pre-defined images can be generated for tissue and stents, features matrices can be computed for each pre-defined image within a training set, and a covariance matrix can be calculated from each feature matrix. A covariance matrix calculated for an input intraluminal image is then compared to the stent and tissue covariance matrices. The training set that minimizes the distance from input intraluminal image indicates a positive detection of the object corresponding to the training set within the input intraluminal image. In addition, a threshold error can be computed for each object, and used to determine if the either object is present in the intravascular image.

Figure 20:
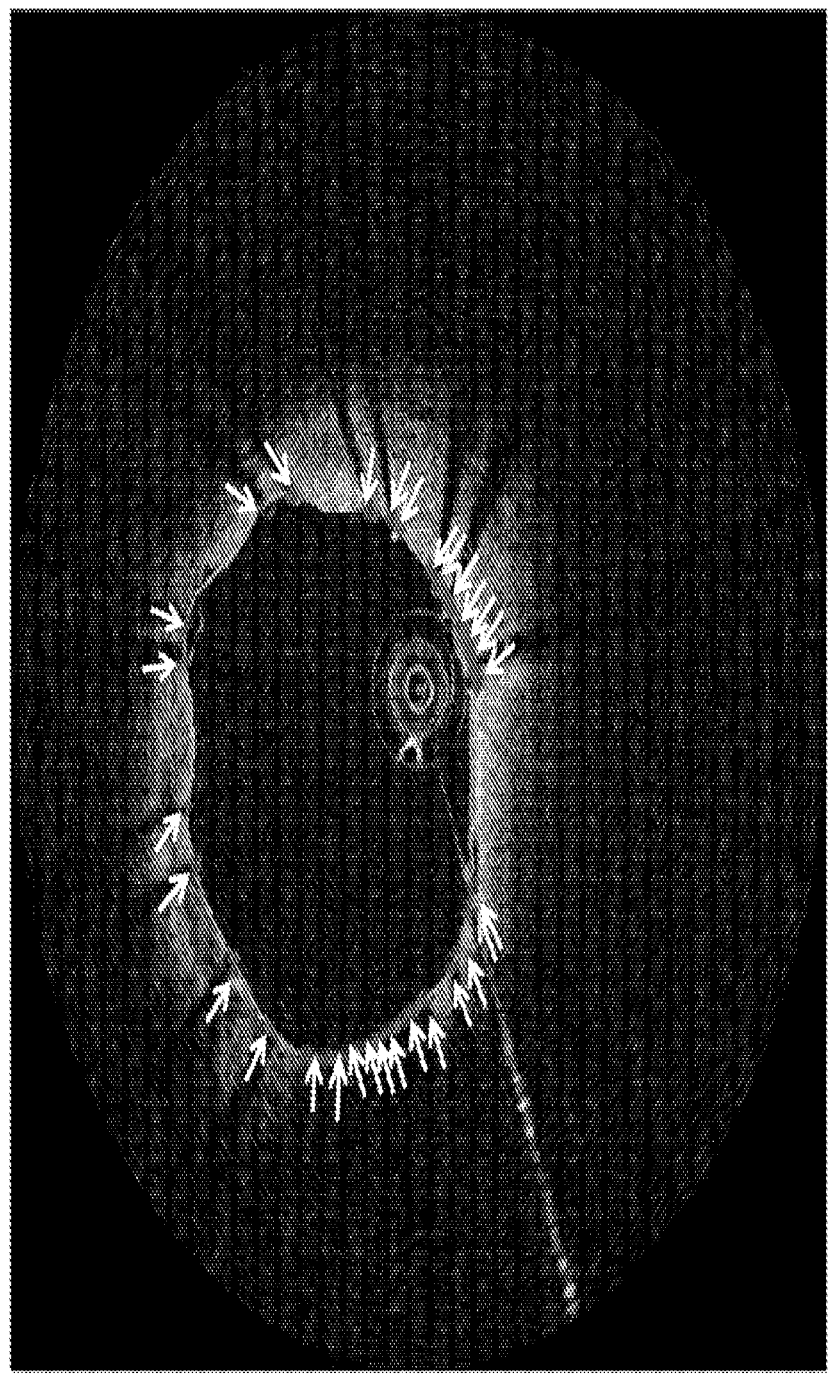
FIG. 20 depicts the resulting stent detections using regional covariance analysis.

FIG. 20 displays detected stent struts within A-scan-converted image using the regional covariance approach. The bolded lines indicate the stent detections. Like the previously discussed embodiments, post-processing can be applied to identify the location of the stent in depth and remove false detections.

In addition, other algorithm image processing techniques known in the art that utilize subspaces for object recognition within images can adapted to detect stents and other objects in intraluminal images. For a concise overview of various object recognition techniques, see Bain and Tao, Chapter 3: "Face Subspace Learning", Handbook of Face Recognition, 2011. For example, Fisher's linear discriminate analysis (FLDA) can be used to detect stents. Linear discriminant analysis is primarily used to reduce the number of features, such as pixel values, to a more manageable number before classification or detection as compared to using principal component analysis. Each of the new dimensions is a linear combination of pixel values, which form a template. The linear combinations obtained using Fisher's linear discriminant is called a linear classifier and can be used in comparison to input intraluminal images to detect stents.

In certain aspects, FDLA can be combined with other algorithmic techniques to improve the accuracy of object detection using the technique. For example, FDLA can be combined with general mean criterion and max-min distance analysis (MMDA), discriminatory locality alignment analysis (DLA), and manifold elastic net (MNE).

Another detection method that can be used or adapted to detect stents or objects in intraluminal images includes using statistical model-based image recognition algorithms. See, for example, Felzenszwalb and Huttenlocher, "Pictorial Structures for Object Recognition," Volume 61, Number 1, 55-79, DOI: 10.1023/B:VISI.0000042934.15159.49; A. A. Amini, T. E. Weymouth, and R. C. Jain. "Using dynamic programming for solving variational problems in vision," IEEE Transactions on Pattern Analysis and Machine Intelligence, 12(9):8551{867, September 1990; M. A. Fischler and R. A. Elschlager, "The representation and matching of pictorial structures," IEEE Transactions on Computer, 22(1):67-92, January 1973.

With respect to the methods of detecting objects within intraluminal images discussed herein, various computer or processor-based systems are suitable for compiling data from intraluminal images, interfacing with an OCT probe to obtain input intraluminal images, applying the disclosed algorithms to detect objects, and displaying the detected objects to a user of the OCT system. The systems and methods of use described herein may take the form of an entirely hardware embodiment, an entirely software embodiment, or an embodiment combining software and hardware aspects. The systems and methods of use described herein can be performed using any type of computing device, such as a computer, that includes a processor or any combination of computing devices where each device performs at least part of the process or method.

In some embodiments, a device of the invention includes an OCT imaging system and obtains a three-dimensional data set through the operation of OCT imaging hardware. In some embodiments, a device of the invention is a computer device such as a laptop, desktop, or tablet computer, and obtains a three-dimensional data set by retrieving it from a tangible storage medium, such as a disk drive on a server using a network or as an email attachment.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Figure 21:
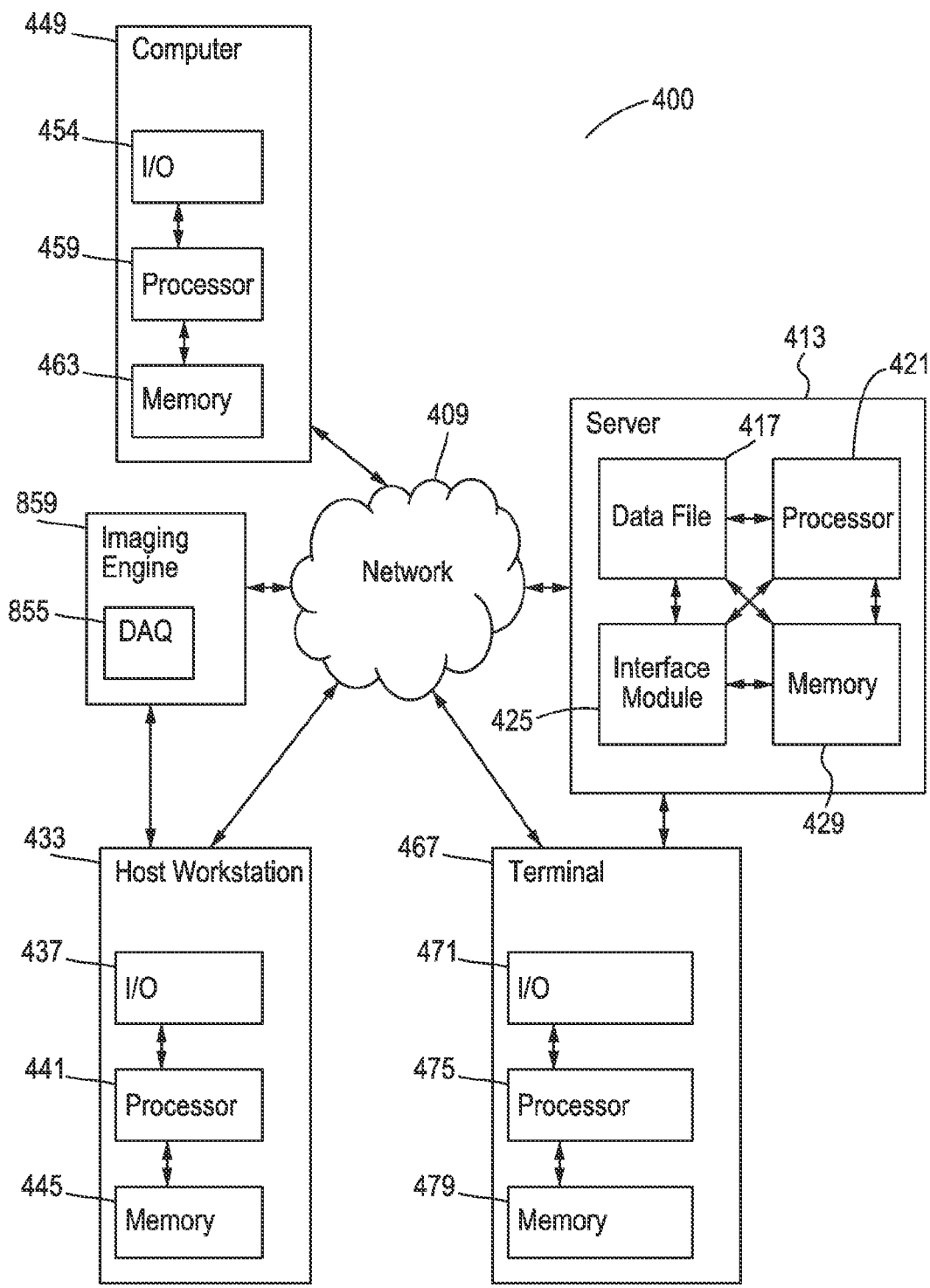
FIG. 21 is a system diagram according to certain embodiments.

In some embodiments, a user interacts with a visual interface to view images from the imaging system. Input from a user (e.g., parameters or a selection) are received by a processor in an electronic device. The selection can be rendered into a visible display. An exemplary system including an electronic device is illustrated in FIG. 21. As shown in FIG. 21, imaging engine 859 communicates with host workstation 433 as well as optionally server 413 over network 409. In some embodiments, an operator uses computer 449 or terminal 467 to control system 400 or to receive images. An image may be displayed using an I/O 454, 437, or 471, which may include a monitor. Any I/O may include a keyboard, mouse or touchscreen to communicate with any of processor 421, 459, 441, or 475, for example, to cause data to be stored in any tangible, nontransitory memory 463, 445, 479, or 429. Server 413 generally includes an interface module 425 to effectuate communication over network 409 or write data to data file 417.

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server 413), a middleware component (e.g., an application server), or a front-end component (e.g., a client computer 449 having a graphical user interface 454 or a web browser through which a user can interact with an implementation of the subject matter described herein), or any combination of such back-end, middleware, and front-end components. The components of the system can be interconnected through network 409 by any form or medium of digital data communication, e.g., a communication network. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a portion of file 417 that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over network 409 (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors.

Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

It will be understood that each block of the FIG. 14, as well as any portion of the systems and methods disclosed herein, can be implemented by computer program instructions. These program instructions may be provided to a processor to produce a machine, such that the instructions, which execute on the processor, create means for implementing the actions specified in the FIG. 14 or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes or even in a different sequence than illustrated without departing from the scope or spirit of the invention.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A computer-readable, non-transitory medium storing software code representing instructions that when executed by a computing system cause the computing system to perform a method of detecting an object within an intraluminal image, the method comprising
   generating a set of pre-defined intraluminal images known to display an object;
   computing principal components for the set to create an object space for the object;
   projecting an input intraluminal image onto the object space; and
   detecting the object in the input intraluminal image,
   wherein the object is selected from the group comprising a stent strut or a guidewire.

2. The computer-readable, non-transitory medium of claim 1, wherein the step of detecting further comprises
   calculating an error between the input intraluminal image and the object space.

3. The computer-readable, non-transitory medium of claim 2, wherein a small error constitutes a positive detection of the object in the input intraluminal image.

4. The computer-readable, non-transitory medium of claim 1, wherein the pre-defined intraluminal images and input intraluminal image are one-dimensional, two-dimensional, or three-dimensional.

5. The computer-readable, non-transitory medium of claim 1, further comprising
   post-processing the input intraluminal image.

6. The computer-readable, non-transitory medium of claim 5, wherein the step of post-processing comprises removing false object detections and highlighting the object detections.

7. The computer-readable, non-transitory medium of claim 1, further comprising
   performing the steps of generating, identifying, and projecting for at least one other object; and
   detecting the at least one other object in the input intraluminal image.

8. The computer-readable, non-transitory medium of claim 7, wherein the step of detecting the at least one other object further comprises
   calculating an error between the input intraluminal image and the object space for the object and between the input intraluminal image and the object space for the at least one other object.

9. The computer-readable, non-transitory medium of claim 7, further wherein the smaller error constitutes a positive detection for the corresponding object.

10. The computer-readable, non-transitory medium of claim 7, wherein the pre-defined intraluminal images and input intraluminal image are one-dimensional, two-dimensional, or three-dimensional.

11. The computer-readable, non-transitory medium of claim 7, wherein the object is selected from the group consisting of a tissue, a stent strut, or a guidewire.

12. The computer-readable, non-transitory medium of claim 7, further comprising
   post-processing the input intraluminal image.

13. The computer-readable, non-transitory medium of claim 12, wherein post-processing comprises removing false object detections and highlighting the object detections.

14. A system for automatically detecting an object within an intraluminal image, comprising:
   a central processing unit (CPU); and
   a storage device coupled to the CPU and having stored there information for configuring the CPU to:
   generate a set of pre-defined intraluminal images known to display a object;
   compute principal components for the set to create an object space for the object; and
   project an input intraluminal data image onto the object space;
   detect the object in the input intraluminal image, wherein the object is selected from the group comprising a stent strut or a guidewire.

15. The system of claim 14, wherein detecting the object further comprises
calculating an error between the input intraluminal image and the object space.

16. The system of claim 15, wherein a small error as compared to the object space constitutes a positive detection of the object in the input intraluminal image.

17. The system of claim 14, wherein the pre-defined intraluminal images and input intraluminal image are one-dimensional, two-dimensional, or three-dimensional.

18. The system of claim 14, further comprising post-processing the input intraluminal image.

19. The system of claim 18, wherein post-processing comprises removing false object detections and highlighting the object detections.

20. The system of claim 14, further comprising
performing the steps of generating, identifying, and projecting for at least one other object; and
detecting the at least one other object in the input intraluminal image.

21. The system of claim 20, wherein the detecting the at least one other object further comprises
calculating an error between the input intraluminal image and the object space for the object and between the input intraluminal image and the object space for the at least one other object.

22. The system of claim 21, further wherein the smaller error constitutes a positive detection for the corresponding object.

23. The system of claim 20, wherein the pre-defined intraluminal images and input intraluminal image are one-dimensional, two-dimensional, or three-dimensional.

24. The system of claim 20, wherein the object is selected from the group consisting of a lumen border, a stent strut, or a guidewire.

25. The system of claim 20, further comprising
post-processing the input intraluminal image.

26. The system of claim 25, wherein post-processing comprises removing false object detections and highlighting the object detections.

27. A computer-readable, non-transitory medium storing software code representing instructions that when executed by a computing system cause the computing system to perform a method of detecting an object within a blood vessel, the method comprising:

generating a training set of pre-defined intraluminal images known to display an object, each intraluminal image comprising a feature;
computing a covariance for a feature within each intraluminal image of the training set; and
detecting the object within an input intraluminal image, the detecting step comprising:
computing a covariance for a feature within the intraluminal input image; and
comparing the covariance of the input intraluminal image to the covariances of the training set to detect the object in the input image,
wherein the object is selected from the group comprising a stent strut or a guidewire.

28. The computer-readable, non-transitory medium of claim 27, wherein a feature is selected from the group consisting of the Cartesian coordinates of a pixel, the intensity at each pixel, and the first and second order derivatives of the image in the x and y direction.

29. The computer-readable, non-transitory medium of claim 27, wherein the pre-defined intraluminal images and input intraluminal image are one-dimensional, two-dimensional, or three-dimensional.

30. A method for detecting an object in an intraluminal image, the method comprising the steps of:
generating a set of pre-defined intraluminal images known to display an object;
computing principal components for the set to create an object space for the object;
projecting an input intraluminal image onto the object space; and
detecting the object in the input intraluminal image,
wherein the object is selected from the group comprising a stent strut or a guidewire.

31. The method of claim 30, further comprising processing the input intraluminal image.

32. The method of claim 31, wherein said processing step processing comprises removing false object detections and highlighting the object detections.

33. The method of claim 30, wherein the step of detecting the at least one other object further comprises calculating an error between the input intraluminal image and the object space for the object and between the input intraluminal image and the object space for the at least one other object.

* * * * *